(12) United States Patent
zur Megede et al.

(10) Patent No.: US 7,622,125 B2
(45) Date of Patent: Nov. 24, 2009

(54) POLYCISTRONIC HIV VECTOR CONSTRUCTS

(75) Inventors: Jan zur Megede, San Francisco, CA (US); Susan W. Barnett, San Francisco, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 262 days.

(21) Appl. No.: 11/124,602

(22) Filed: May 5, 2005

(65) Prior Publication Data

US 2005/0287167 A1    Dec. 29, 2005

Related U.S. Application Data

(60) Provisional application No. 60/568,390, filed on May 5, 2004.

(51) Int. Cl.
*A61K 39/12* (2006.01)
*A61K 39/21* (2006.01)
*C07H 21/02* (2006.01)
*C07H 21/04* (2006.01)

(52) U.S. Cl. ............... 424/204.1; 424/205.1; 424/207.1; 424/208.1; 536/23.1; 536/23.4; 536/23.7; 536/23.72

(58) Field of Classification Search ........................ None
See application file for complete search history.

(56) References Cited

U.S. PATENT DOCUMENTS

| | | | |
|---|---|---|---|
| 5,585,263 A * | 12/1996 | Hammarskjold et al. | ... 435/236 |
| 5,789,245 A | 8/1998 | Dubensky, Jr. | |
| 5,814,482 A | 9/1998 | Dubensky, Jr. | |
| 5,837,464 A * | 11/1998 | Capon et al. | .................... 435/6 |
| 5,840,313 A | 11/1998 | Vahlne | |
| 5,843,723 A | 12/1998 | Dubensky, Jr. | |
| 5,846,546 A | 12/1998 | Hurwitz | |
| 5,876,731 A | 3/1999 | Sia | |
| 6,323,030 B1 | 11/2001 | Stemmer | |
| 6,376,235 B1 | 4/2002 | Beattie | |
| 6,413,774 B1 | 7/2002 | Stemmer | |
| 6,420,175 B1 | 7/2002 | Stemmer | |
| 6,444,468 B1 | 9/2002 | Stemmer | |
| 6,602,705 B1 | 8/2003 | Barnett | |
| 6,689,879 B2 | 2/2004 | Barnett | |
| 2003/0148262 A1 | 8/2003 | Polo | |
| 2003/0175292 A1 * | 9/2003 | Robinson et al. | ......... 424/188.1 |
| 2003/0232324 A1 | 12/2003 | Polo | |

FOREIGN PATENT DOCUMENTS

| | | |
|---|---|---|
| WO | WO 95/07995 | 3/1995 |
| WO | WO 96/17072 | 6/1996 |
| WO | WO 00/39302 | 7/2000 |
| WO | WO 00/39303 | 7/2000 |
| WO | WO 00/39304 | 7/2000 |
| WO | WO 02/00250 | 1/2002 |
| WO | WO 02/04493 | 1/2002 |
| WO | WO 02/099035 | 12/2002 |
| WO | WO 03/004620 | 1/2003 |
| WO | WO 03/004657 | 1/2003 |
| WO | WO 03/020876 | 3/2003 |

OTHER PUBLICATIONS

GenBank Accession No. K02007 (Aug. 11, 1995).
GenBank Accsssion No. M38428 (Aug. 2, 1993).
GenBank Accession No. AF110965 (Oct. 15, 2001).
GenBank Accession No. AF110975 (Oct. 15, 2001).
Dubensky et al., "Sindbis Virus DNA-Based Expression Vectors: Utility for In Vitro and In Vivo Gene Transfer," J. Virol. (1996) 70:508-519.

* cited by examiner

*Primary Examiner*—Jeffrey S Parkin
*Assistant Examiner*—Louise Humphrey
(74) *Attorney, Agent, or Firm*—Regina Bautista; Helen Lee

(57) ABSTRACT

The present disclosure relates to vectors comprising polynucleotide sequences that encode HIV polypeptides. In particular, the disclosure relates polycistronic vector constructs comprising sequences that encode HIV polypeptides as a single polyprotein. Compositions comprising these vectors and sequences along with methods of using these vectors and sequences are also disclosed.

32 Claims, 10 Drawing Sheets

FIGURE 1: TRNgagCpolIna (with ATIM/MQR HIV protease cleavage site between TRN and gagCpolIna)(SEQ ID NO:1)

```
gtcgacgccaccatggagcccgtggaccccgcctggagccctggaagcaccccggcag
ccagcccaagaccgccggcaccaactgctactgcaagaagtgctgcttccactgccagg
tgagcttcatcaccaagggcctgggcatcagctacggccgcaagaagcgccgccagcgc
cgccgcgccccccgacagcgaggtgcaccaggtgagcctgcccaagcagcccgccag
ccagccccagggcgaccccaccggccccaaggagagcaagaagaaggtggagcgcgaga
ccgagaccgacccgtgcacgaattcgccggccgcagcggcgacagcgacgaggagctg
ctgcagaccgtgcgcttcatcaagttcctgtaccagagcaacccctgcccagccccaa
gggcacccgccaggccgacctgaaccgccgccgcgctggcgcgagcgccagcgccaga
tccagagcatcagcgcctggatcatcagcacccacctgggccgcagcaccgagcccgtg
cccctgcagctgccccccgacctgcgcctgaacctggactgcagcgaggactgcggcac
cagcggcacccagggcgtgggcagcccccaggtgctgggcgagagccccgccgtgctgg
acagcggcaccaaggagctcgaggccggcaagtggagcaagcgcatgagcggctggagc
gccgtgcgcgagcgcatgaagcgcgccgagcccgccgagcccgccgccgacggcgtggg
cgccgtgagccgcgacctggagaagcacggcgccatcaccagcagcaacaccgccgcca
acaacgccgactgcgcctggctggaggcccaggaggacgaggacgtgggcttccccgtg
cgccccaggtgcccctgcgccccatgacctacaaggccgccctggacctgagccactt
cctgaaggagaagggcggcctggagggcctgatctacagccagaagcgccaggacatcc
tggacctgtggatccaccacacccagggctacttccccggctggcagaactacaccccc
ggccccggcatccgctaccccctgaccttcggctggtgcttcaagctggtgcccgtgga
ccccgactacgtggaggaggccaacgccggcgagaacaacagcctgctgcacccatga
gccagcacggcatggacgaccccgagaaggaggtgctggtgtggcgcttcgacagccgc
ctggccttccaccacatggcccgcgagctgcaccccgagtactacaaggactgcgctac
tatcatgatgcagcgctctagaggcgcccgcgccagcgtgctgagcggcggcgagctgg
acaagtgggagaagatccgcctgcgccccggcggcaagaagaagtacaagctgaagcac
atcgtgtgggccagccgcgagctggagcgcttcgccgtgaaccccggcctgctggagac
cagcgagggctgccgccagatcctgggccagctgcagcccagcctgcagaccggcagcg
aggagctgcgcagcctgtacaacaccgtggccaccctgtactgcgtgcaccagcgcatc
gacgtcaaggacaccaaggaggccctggagaagatcgaggaggagcagaacaagtccaa
gaagaaggcccagcaggccgccgccgccgccggcaccggcaacagcagccaggtgagcc
agaactaccccatcgtgcagaacctgcagggccagatggtgcaccaggccatcagcccc
cgcacccgaacgcctgggtgaaggtggtggaggagaaggccttcagccccgaggtgat
ccccatgttcagcgccctgagcgagggcgccacccccaggacctgaacacgatgttga
acaccgtgggcggccaccaggccgccatgcagatgctgaaggagaccatcaacgaggag
gccgccgagtgggaccgcgtgcaccccgtgcacgccggccccatcgcccccggccagat
gcgcgagccccgcggcagcgacatcgccggcaccaccagcacccrgcaggagcagatcg
gctggatgaccaacaaccccccatccccgtgggcgagatctacaagcggtggatcatc
ctgggcctgaacaagatcgtgcggatgtacagccccaccagcatcctggacatccgcca
gggccccaaggagcccttccgcgactacgtggaccgcttctacaagaccctgcgcgctg
agcaggccagccaggacgtgaagaactggatgaccgagaccctgctggtgcagaacgcc
aacccccgactgcaagaccatcctgaaggctctcggccccgcggccaccctggaggagat
gatgaccgcctgccagggcgtgggcggcccggccacaaggcccgcgtgctggccgagg
cgatgagccaggtgacgaacccggcgaccatcatgatgcagcgcggcaacttccgcaac
cagcggaagaccgtcaagtgcttcaactgcggcaaggagggccacaccgccaggaactg
ccgcgccccccgcaagaagggctgctggcgctgcggccgcgagggccaccagatgaagg
```

FIGURE 1A

```
actgcaccgagcgccaggccaacttcctgggcaagatctggcccagctacaagggccgc
cccggcaacttcctgcagagccgccccgagcccaccgcccccccgaggagagcttccg
cttcggcgaggagaagaccaccccccagccagaagcaggagcccatcgacaaggagctgt
accccctgaccagcctgcgcagcctgttcggcaacgaccccagcagccagaaagaattc
aaggcccgcgtgctggccgaggcgatgagccaggtgacgaacccggcgaccatcatgat
gcagcgcggcaacttccgcaaccagcggaagaccgtcaagtgcttcaactgcggcaagg
agggccacaccgccaggaactgccgcgccccccgcaagaagggctgctggcgctgcggc
cgcgaaggacaccaaatgaaagattgcactgagagacaggctaatttcttccgcgagga
cctggccttcctgcagggcaaggcccgcgagttcagcagcgagcagacccgcgccaaca
gccccacccgccgcgagctgcaggtgtggggcggcgagaacaacagcctgagcgaggcc
ggcgccgaccgccagggcaccgtgagcttcaacttcccccagatcaccctgtggcagcg
ccccctggtgaccatcaggatcggcggccagctcaaggaggcgctgctcgccaccggcg
ccgacgacaccgtgctggaggagatgaacctgccggcaagtggaagcccaagatgatc
ggcgggatcggggggcttcatcaaggtgcggcagtacgaccagatccccgtggagatctg
cggccacaaggccatcggcaccgtgctggtgggcccaccccgtgaacatcatcggcc
gcaacctgctgacccagatcggctgcaccctgaacttccccatcagccccatcgagacg
gtgcccgtgaagctgaagccggggatggacggccccaaggtcaagcagtggccccctgac
cgaggagaagatcaaggccctggtggagatctgcaccgagatggagaaggagggcaaga
tcagcaagatcggccccgagaaccccctacaacaccccgtgttcgccatcaagaagaag
gacagcaccaagtggcgcaagctggtggacttccgcgagctgaacaagcgcacccagga
cttctgggaggtgcagctgggcatccccaccccgccggcctgaagaagaagaagagcg
tgaccgtgctggacgtgggcgacgcctacttcagcgtgcccctggacaaggacttccgc
aagtacaccgccttcaccatccccagcatcaacaacgagacccccggcatccgctacca
gtacaacgtgctgccccagggctggaagggcagcccgccatcttccagagcagcatga
ccaagatcctggagcccttccgcaagcagaaccccgacatcgtgatctaccaggccccc
ctgtacgtgggcagcgacctggagatcggccagcaccgcaccaagatcgaggagctgcg
ccagcacctgctgcgctggggcttcaccaccccgacaagaagcaccagaaggagcccc
ccttcctgcccatcgagctgcaccccgacaagtggaccgtgcagcccatcatgctgccc
gagaaggacagctggaccgtgaacgacatccagaagctggtgggcaagctgaactgggc
cagccagatctacgccggcatcaaggtgaagcagctgtgcaagctgctgcgcggcacca
aggccctgaccgaggtgatccccctgaccgaggaggccgagctggagctggccgagaac
cgcgagatcctgaaggagcccgtgcacgaggtgtactacgaccccagcaaggacctggt
ggccgagatccagaagcagggccagggcagtggacctaccagatctaccaggagccct
tcaagaacctgaagaccggcaagtacgcccgcatgcgcggcgcccacaccaacgacgtg
aagcagctgaccgaggccgtgcagaaggtgagcaccgagagcatcgtgatctggggcaa
gatccccaagttcaagctgcccatccagaaggagacctgggaggcctggtggatggagt
actggcaggccacctggatccccgagtgggagttcgtgaacaccccccccctggtgaag
ctgtggtaccagctggagaaggagcccatcgtgggcgccgagaccttctacgtggacgg
cgccgccaaccgcgagaccaagctgggcaaggccggctacgtgaccgaccggggccggc
agaaggtggtgagcatcgccgacaccaccaaccagaagaccgagctgcaggccatccac
ctggccctgcaggacagcggcctggaggtgaacatcgtgaccgacagccagtacgccct
gggcatcatccaggcccagcccgacaagagcgagagcgagctggtgagccagatcatcg
agcagctgatcaagaaggagaaggtgtacctggcctgggtgcccgcccacaagggcatc
ggcggcaacgagcaggtggacaagctggtgagcgccggcatccgcaaggtgctgttcct
gaacggcatcgatggcggcatcgtgatctaccagtacatggacgacctgtacgtgggca
gcggcggccctaggatcgattaaaagcttcccggggctagcaccggttctaga
```

FIGURE 1B

FIGURE 2: gagCpolInaTRN (SEQ ID NO:2)

```
gtcgacgccaccatgggcgcccgcgccagcgtgctgagcggcggcgagctggacaagtg
ggagaagatccgcctgcgccccggcggcaagaagaagtacaagctgaagcacatcgtgt
gggccagccgcgagctggagcgcttcgccgtgaaccccggcctgctggagaccagcgag
ggctgccgccagatcctgggccagctgcagcccagcctgcagaccggcagcgaggagct
gcgcagcctgtacaacaccgtggccaccctgtactgcgtgcaccagcgcatcgacgtca
aggacaccaaggaggccctggagaagatcgaggaggagcagaacaagtccaagaagaag
gcccagcaggccgccgccgccgcggcaccggcaacagcagccaggtgagccagaacta
ccccatcgtgcagaacctgcagggccagatggtgcaccaggccatcagccccgcaccc
tgaacgcctgggtgaaggtggtggaggagaaggccttcagccccgaggtgatccccatg
ttcagcgccctgagcgagggcgccaccccccaggacctgaacacgatgttgaacaccgt
gggcggccaccaggccgccatgcagatgctgaaggagaccatcaacgaggaggccgccg
agtgggaccgcgtgcaccccgtgcacgccggccccatcgcccccggccagatgcgcgag
ccccgcggcagcgacatcgccggcaccaccagcaccctgcaggagcagatcggctggat
gaccaacaacccccccatccccgtgggcgagatctacaagcggtggatcatcctgggcc
tgaacaagatcgtgcggatgtacagccccaccagcatcctggacatccgccagggcccc
aaggagcccttccgcgactacgtggaccgcttctacaagaccctgcgcgctgagcaggc
cagccaggacgtgaagaactggatgaccgagaccctgctggtgcagaacgccaaccccg
actgcaagaccatcctgaaggctctcggccccgcggccaccctggaggagatgatgacc
gcctgccagggcgtgggcggccccggccacaaggcccgcgtgctggccgaggcgatgag
ccaggtgacgaacccggcgaccatcatgatgcagcgcggcaacttccgcaaccagcgga
agaccgtcaagtgcttcaactgcggcaaggagggccacaccgccaggaactgccgcgcc
ccccgcaagaagggctgctggcgctgcggccgcgagggccaccagatgaaggactgcac
cgagcgccaggccaacttcctgggcaagatctggccagctacaagggccgccccggca
acttcctgcagagccgccccgagcccaccgccccccccgaggagagcttccgcttcggc
gaggagaagaccaccccagccagaagcaggagcccatcgacaaggagctgtacccct
gaccagcctgcgcagcctgttcggcaacgaccccagcagccagaaagaattcaaggccc
gcgtgctggccgaggcgatgagccaggtgacgaacccggcgaccatcatgatgcagcgc
ggcaacttccgcaaccagcggaagaccgtcaagtgcttcaactgcggcaaggagggcca
caccgccaggaactgccgcgccccccgcaagaagggctgctggcgctgcggccgcgaag
gacaccaaatgaaagattgcactgagagacaggctaatttcttccgcgaggacctggcc
ttcctgcagggcaaggcccgcgagttcagcagcgagcagacccgcgccaacagccccac
ccgccgcgagctgcaggtgtggggcggcgagaacaacagcctgagcgaggccggcgccg
accgccagggcaccgtgagcttcaacttcccccagatcaccctgtggcagcgccccctg
gtgaccatcaggatcggcggccagctcaaggaggcgctgctcgccaccggcgccgacga
caccgtgctggaggagatgaacctgcccggcaagtggaagcccaagatgatcggcggga
tcgggggcttcatcaaggtgcggcagtacgaccagatccccgtggagatctgcggccac
aaggccatcggcaccgtgctggtgggcccaccccgtgaacatcatcggccgcaacct
gctgacccagatcggctgcaccctgaacttccccatcagccccatcgagacggtgcccg
tgaagctgaagccggggatggacggccccaaggtcaagcagtggcccctgaccgaggag
aagatcaaggcctggtggagatctgcaccgagatggagaaggagggcaagatcagcaa
gatcggccccgagaacccctacaacaccccgtgttcgccatcaagaagaaggacagca
ccaagtggcgcaagctggtggacttccgcgagctgaacaagcgcacccaggacttctgg
gaggtgcagctgggcatccccacccgccggcctgaagaagaagaagagcgtgaccgt
gctggacgtgggcgacgcctacttcagcgtgcccctggacaaggacttccgcaagtaca
```

FIGURE 2A

```
ccgccttcaccatccccagcatcaacaacgagaccccggcatccgctaccagtacaac
gtgctgccccagggctggaagggcagccccgccatcttccagagcagcatgaccaagat
cctggagcccttccgcaagcagaaccccgacatcgtgatctaccaggccccctgtacg
tgggcagcgacctggagatcggccagcaccgcaccaagatcgaggagctgcgccagcac
ctgctgcgctggggcttcaccaccccgacaagaagcaccagaaggagccccccttcct
gcccatcgagctgcaccccgacaagtggaccgtgcagcccatcatgctgcccgagaagg
acagctggaccgtgaacgacatccagaagctggtgggcaagctgaactgggccagccag
atctacgccggcatcaaggtgaagcagctgtgcaagctgctgcgcggcaccaaggccct
gaccgaggtgatcccctgaccgaggaggccgagctggagctggccgagaaccgcgaga
tcctgaaggagcccgtgcacgaggtgtactacgaccccagcaaggacctggtggccgag
atccagaagcagggccagggccagtggacctaccagatctaccaggagcccttcaagaa
cctgaagaccggcaagtacgcccgcatgcgcggcgcccacaccaacgacgtgaagcagc
tgaccgaggccgtgcagaaggtgagcaccgagagcatcgtgatctggggcaagatcccc
aagttcaagctgcccatccagaaggagacctggaggcctggtggatggagtactggca
ggccacctggatccccgagtgggagttcgtgaacaccccccccctggtgaagctgtggt
accagctggagaaggagcccatcgtgggcgccgagaccttctacgtggacggcgccgcc
aaccgcgagaccaagctgggcaaggccggctacgtgaccgaccggggccggcagaaggt
ggtgagcatcgccgacaccaccaaccagaagaccgagctgcaggccatccacctggccc
tgcaggacagcggcctggaggtgaacatcgtgaccgacagccagtacgccctgggcatc
atccaggcccagcccgacaagagcgagagcgagctggtgagccagatcatcgagcagct
gatcaagaaggagaaggtgtacctggcctgggtgcccgcccacaagggcatcggcggca
acgagcaggtggacaagctggtgagcgccggcatccgcaaggtgctgttcctgaacggc
atcgatggcggcatcgtgatctaccagtacatggacgacctgtacgtgggcagcggcgg
ccctaggatcgatgagcccgtggaccccgcctggagccctggaagcaccccggcagcc
agcccaagaccgccggcaccaactgctactgcaagaagtgctgcttccactgccaggtg
agcttcatcaccaagggcctgggcatcagctacggccgcaagaagcgccgccagcgccg
ccgcgccccccccgacagcgaggtgcaccaggtgagcctgcccaagcagcccgccagcc
agccccagggcgacccaccggccccaaggagagcaagaagaaggtggagcgcgagacc
gagaccgaccccgtgcacgaattcgccggccgcagcggcgacagcgacgaggagctgct
gcagaccgtgcgcttcatcaagttcctgtaccagagcaaccccctgcccagccccaagg
gcacccgccaggccgacctgaaccgccgccgccgctggcgcgagcgccagcgccagatc
cagagcatcagcgcctggatcatcagcacccacctgggccgcagcaccgagcccgtgcc
cctgcagctgcccccgacctgcgcctgaacctggactgcagcgaggactgcggcacca
gcggcacccagggcgtgggcagccccaggtgctgggcgagagccccgccgtgctggac
agcggcaccaaggagctcgaggccggcaagtggagcaagcgcatgagcggctggagcgc
cgtgcgcgagcgcatgaagcgcgccgagcccgcgagcccgccgcgacggcgtgggcg
ccgtgagccgcgacctggagaagcacggcgccatcaccagcagcaacaccgccgccaac
aacgccgactgcgcctggctggaggcccaggaggacgaggacgtgggcttccccgtgcg
ccccaggtgcccctgcgccccatgacctacaaggccgccctggacctgagccacttcc
tgaaggagaagggcggcctggagggcctgatctacagccagaagcgccaggacatcctg
gacctgtggatccaccacacccagggctacttccccggctggcagaactacaccccgg
ccccggcatccgctaccccctgaccttcggctggtgcttcaagctggtgcccgtggacc
ccgactacgtggaggaggccaacgccggcgagaacaacagcctgctgcaccccatgagc
cagcacggcatggacgaccccgagaaggaggtgctggtgtggcgcttcgacagccgcct
ggccttccaccacatggcccgcgagctgcaccccgagtactacaaggactgcgcttaag
cttcccggggctagcaccggttctaga
```

FIGURE 2B

SEQUENCE LISTING

<160> NUMBER OF SEQ ID NOS: 2

<210> SEQ ID NO 1
<211> LENGTH: 5304
<212> TYPE: DNA
<213> ORGANISM: Artificial
<220> FEATURE:
<223> OTHER INFORMATION: TRNgagCpolIna

<400> SEQUENCE: 1

```
gtcgacgcca ccatggagcc cgtggacccc cgcctggagc cctggaagca ccccggcagc      60
cagcccaaga ccgccggcac caactgctac tgcaagaagt gctgcttcca ctgccaggtg     120
agcttcatca ccaaggcct gggcatcagc tacgccgca agaagcgccg ccagcgccgc      180
cgcgcccccc ccgacagcga ggtgcaccag gtgagcctgc ccaagcagcc cgccagccag     240
ccccagggcg acccaccgg ccccaaggag agcaagaaga aggtggagcg cgagaccgag      300
accgaccccg tgcacgaatt cgccggccgc agcggcgaca cgacgagga gctgctgcag     360 accgtgcgct tcatcaagtt cctgtaccag agcaacccc tgcccagccc caagggcacc     420
cgccaggccg acctgaaccg ccgccgccgc tggcgcgagc gccagcgcca gatccagagc     480
atcagcgcct ggatcatcag cacccacctg ggccgcagca ccgagcccgt gccctgcag     540 ctgcccccg acctgcgcct gaacctggac tgcagcgagg actgcggcac cagcggcacc     600
cagggcgtgg gcagccccca ggtgctgggc gagagccccg ccgtgctgga cagcggcacc     660
aaggagctcg aggccggcaa gtggagcaag cgcatgagcg gctggagcgc cgtgcgcgag     720
cgcatgaagc gcgccgagcc cgccgagccc gccgccgacg gcgtgggcgc cgtgagccgc     780
gacctggaga agcacggcgc catcaccagc agcaacaccg ccgccaacaa cgccgactgc     840
gcctggctgg aggccccagga ggacgaggac gtgggcttcc ccgtgcgccc ccaggtgccc     900
ctgcgcccca tgacctacaa ggccgccctg gacctgagcc acttcctgaa ggagaagggc     960
ggcctggagg gcctgatcta cagccagaag cgccaggaca tcctggacct gtggatccac    1020
cacacccagg gctacttccc cggctggcag aactacaccc ccggccccgg catccgctac    1080 ccctgacct cggctggtg cttcaagctg gtgcccgtgg accccgacta cgtggaggag    1140
gccaacgccg gcgagaacaa cagcctgctg caccccatga gccagcacgg catggacgac    1200
cccgagaagg aggtgctggt gtggcgcttc gacagccgcc tggccttcca ccacatggcc    1260
cgcgagctgc accccgagta ctacaaggac tgcgctacta tcatgatgca gcgctctaga    1320
ggcgcccgcg ccagcgtgct gagcggcggc gagctggaca agtgggagaa gatccgcctg    1380
cgccccggcg gcaagaagaa gtacaagctg aagcacatcg tgtgggccag ccgcgagctg    1440
gagcgcttcg ccgtgaaccc cggcctgctg gagaccagcg agggctgccg ccagatcctg    1500
```

```
ggccagctgc agcccagcct gcagaccggc agcgaggagc tgcgcagcct gtacaacacc    1560
gtggccaccc tgtactgcgt gcaccagcgc atcgacgtca aggacaccaa ggaggccctg    1620
gagaagatcg aggaggagca gaacaagtcc aagaagaagg cccagcaggc cgccgccgcc    1680
gccggcaccg gcaacagcag ccaggtgagc cagaactacc ccatcgtgca gaacctgcag    1740
ggccagatgg tgcaccaggc catcagcccc cgcacccctga acgcctgggt gaaggtggtg    1800
gaggagaagg ccttcagccc cgaggtgatc cccatgttca cgcccctgag cgagggcgcc    1860
accccccagg acctgaacac gatgttgaac accgtgggcg ccaccaggcc gccatgcag     1920 atgctgaagg agaccatcaa cgaggaggcc gccgagtggg accgcgtgca ccccgtgcac    1980
gccggcccca tcgcccccgg ccagatgcgc gagccccgcg cagcgacat cgccggcacc     2040 accagcaccc tgcaggagca gatcggctgg atgaccaaca ccccccat ccccgtgggc      2100 gagatctaca agcggtggat catcctgggc ctgaacaaga tcgtgcggat gtacagcccc   2160
accagcatcc tggacatccg ccagggcccc aaggagccct tccgcgacta cgtggaccgc    2220
ttctacaaga ccctgcgcgc tgagcaggcc agccaggacg tgaagaactg gatgaccgag    2280
accctgctgg tgcagaacgc caaccccgac tgcaagacca ccctgaaggc tctcggcccc    2340
gcggccaccc tggaggagat gatgaccgcc tgccagggcg tgggcggccc cggccacaag    2400
gcccgcgtgc tggccgaggc gatgagccag gtgacgaacc cggcgaccat catgatgcag    2460
cgcggcaact tccgcaacca gcggaagacc gtcaagtgct tcaactgcgg caaggagggc    2520
cacaccgcca ggaactgccg cgccccccgc aagaagggct gctggcgctg cggccgcgag    2580
ggccaccaga tgaaggactg caccgagcgc caggccaact tcctgggcaa gatctggccc    2640
agctacaagg gccgccccgg caacttcctg cagagccgcc ccgagcccac cgccccccc     2700 gaggagagct tccgcttcgg cgaggagaag accaccccca gccagaagca ggagcccatc    2760
gacaaggagc tgtaccccct gaccagcctg cgcagcctgt tcggcaacga ccccagcagc    2820
cagaaagaat tcaaggcccg cgtgctggcc gaggcgatga gccaggtgac gaacccggcg    2880
accatcatga tgcagcgcgg caacttccgc aaccagcgga gaccgtcaa gtgcttcaac    2940 tgcggcaagg agggccacac cgccaggaac tgccgcgccc ccgcaagaa gggctgctgg    3000 cgctgcggcc gcgaaggaca ccaaatgaaa gattgcactg agagacaggc taatttcttc    3060
cgcgaggacc tggccttcct gcagggcaag gcccgcgagt cagcagcga gcagacccgc     3120 gccaacagcc ccacccgccg cgagctgcag gtgtggggcg gcgagaacaa cagcctgagc    3180
gaggccggcg ccgaccgcca gggcaccgtg agcttcaact tccccagat cacctgtgg     3240 cagcgccccc tggtgaccat caggatcggc ggccagctca aggaggcgct gctcgccacc    3300
ggcgccgacg acaccgtgct ggaggagatg aacctgcccg gcaagtggaa gcccaagatg    3360
atcggcggga tcgggggctt catcaaggtg cggcagtacg accagatccc cgtggagatc    3420
tgcggccaca aggccatcgg caccgtgctg gtgggcccca ccccgtgaa catcatcggc    3480 cgcaacctgc tgacccagat cggctgcacc ctgaacttcc ccatcagccc catcgagacg    3540
gtgcccgtga agctgaagcc ggggatggac ggccccaagg tcaagcagtg gcccctgacc    3600
gaggagaaga tcaaggccct ggtggagatc tgcaccgaga tggagaagga gggcaagatc    3660
agcaagatcg cccccgagaa ccctacaac accccccgtgt cgccatcaa gaagaaggac    3720 agcaccaagt ggcgcaagct ggtggacttc cgcgagctga acaagcgcac ccaggacttc    3780
tgggaggtgc agctgggcat cccccacccc gccggcctga agaagaagaa gagcgtgacc    3840
gtgctggacg tgggcgacgc ctacttcagc gtgcccctgg acaaggactt ccgcaagtac    3900
```

| | |
|---|---|
| accgccttca ccatccccag catcaacaac gagaccccg gcatccgcta ccagtacaac | 3960 |
| gtgctgcccc agggctggaa gggcagcccc gccatcttcc agagcagcat gaccaagatc | 4020 |
| ctggagccct tccgcaagca gaaccccgac atcgtgatct accaggcccc cctgtacgtg | 4080 |
| ggcagcgacc tggagatcgg ccagcaccgc accaagatcg aggagctgcg ccagcacctg | 4140 |
| ctgcgctggg gcttcaccac ccccgacaag aagcaccaga aggagccccc cttcctgccc | 4200 |
| atcgagctgc accccgacaa gtggaccgtg cagcccatca tgctgcccga aggacagc | 4260 |
| tggaccgtga cgacatcca gaagctggtg ggcaagctga actgggccag ccagatctac | 4320 |
| gccggcatca aggtgaagca gctgtgcaag ctgctgcgcg gcaccaaggc cctgaccgag | 4380 |
| gtgatccccc tgaccgagga ggccgagctg agctggccg agaaccgcga gatcctgaag | 4440 |
| gagcccgtgc acgaggtgta ctacgacccc agcaaggacc tggtggccga gatccagaag | 4500 |
| cagggccagg gccagtggac ctaccagatc taccaggagc ccttcaagaa cctgaagacc | 4560 |
| ggcaagtacg cccgcatgcg cggcgcccac accaacgacg tgaagcagct gaccgaggcc | 4620 |
| gtgcagaagg tgagcaccga gagcatcgtg atctggggca agatccccaa gttcaagctg | 4680 |
| cccatccaga aggagacctg ggaggcctgg tggatggagt actggcaggc cacctggatc | 4740 |
| cccgagtggg agttcgtgaa cacccccccc ctggtgaagc tgtggtacca gctggagaag | 4800 |
| gagcccatcg tgggcgccga gaccttctac gtggacggcg ccgccaaccg cgagaccaag | 4860 |
| ctgggcaagg ccggctacgt gaccgaccgg ggccggcaga aggtggtgag catcgccgac | 4920 |
| accaccaacc agaagaccga gctgcaggcc atccacctgg ccctgcagga cagcggcctg | 4980 |
| gaggtgaaca tcgtgaccga cagccagtac gccctgggca tcatccaggc ccagcccgac | 5040 |
| aagagcgaga gcgagctggt gagccagatc atcgagcagc tgatcaagaa ggagaaggtg | 5100 |
| tacctggcct gggtgcccgc ccacaagggc atcggcggca acgagcaggt ggacaagctg | 5160 |
| gtgagcgccg catccgcaa ggtgctgttc ctgaacggac tcgatggcgg catcgtgatc | 5220 |
| taccagtaca tggacgacct gtacgtgggc agcggcggcc ctaggatcga ttaaaagctt | 5280 |
| cccggggcta gcaccggttc taga | 5304 |

<210> SEQ ID NO 2
<211> LENGTH: 5278
<212> TYPE: DNA
<213> ORGANISM: Artificial
<220> FEATURE:
<223> OTHER INFORMATION: gagCpolInaTRN

<400> SEQUENCE: 2

| | |
|---|---|
| gtcgacgcca ccatgggcgc ccgcgccagc gtgctgagcg gcggcgagct ggacaagtgg | 60 |
| gagaagatcc gcctgcgccc cggcggcaag aagaagtaca agctgaagca catcgtgtgg | 120 |
| gccagccgcg agctggagcg cttcgccgtg aaccccggcc tgctggagac cagcgagggc | 180 |
| tgccgccaga tcctgggcca gctgcagccc agcctgcaga ccggcagcga ggagctgcgc | 240 |
| agcctgtaca acaccgtggc caccctgtac tgcgtgcacc agcgcatcga cgtcaaggac | 300 |
| accaaggagg ccctggagaa gatcgaggag gagcagaaca agtccaagaa gaaggcccag | 360 |
| cagccgccg ccgccgccgg caccggcaac agcagccagg tgagcagaa ctaccccatc | 420 |
| gtgcagaacc tgcagggcca gatggtgcac caggccatca gccccgcac cctgaacgcc | 480 |
| tgggtgaagg tggtgagga aaggccttc agccccgagg tgatccccat gttcagcgcc | 540 |
| ctgagcgagg gcgccacccc ccaggacctg aacacgatgt tgaacaccgt gggcggccac | 600 |

-continued

```
caggccgcca tgcagatgct gaaggagacc atcaacgagg aggccgccga gtgggaccgc    660
gtgcaccccg tgcacgccgg ccccatcgcc cccggccaga tgcgcgagcc ccgcggcagc    720
gacatcgccg gcaccaccag caccctgcag gagcagatcg gctggatgac caacaacccc    780
cccatccccg tgggcgagat ctacaagcgg tggatcatcc tgggcctgaa caagatcgtg    840
cggatgtaca gccccaccag catcctggac atccgccagg gccccaagga gcccttccgc    900
gactacgtgg accgcttcta caagaccctg cgcgctgagc aggccagcca ggacgtgaag    960
aactggatga ccgagaccct gctggtgcag aacgccaacc ccgactgcaa gaccatcctg   1020
aaggctctcg gccccgcggc caccctggag gagatgatga ccgcctgcca gggcgtgggc   1080
ggccccggcc acaaggcccg cgtgctggcc gaggcgatga gccaggtgac gaacccggcg   1140
accatcatga tgcagcgcgg caacttccgc aaccagcgga agaccgtcaa gtgcttcaac   1200
tgcggcaagg agggccacac cgccaggaac tgccgcgccc ccgcaagaa gggctgctgg   1260 cgctgcggcc gcgagggcca ccagatgaag gactgcaccg agcgccaggc caacttcctg   1320
ggcaagatct ggcccagcta aagggccgc cccggcaact tcctgcagag ccgccccgag   1380
cccaccgccc cccccgagga gagcttccgc ttcggcgagg agaagaccac ccccagccag   1440
aagcaggagc ccatcgacaa ggagctgtac cccctgacca gcctgcgcag cctgttcggc   1500
aacgacccca gcagcagaa agaattcaag gcccgcgtgc tggccgaggc gatgagccag   1560
gtgacgaacc cggcgaccat catgatgcag cgcggcaact tccgcaacca gcggaagacc   1620
gtcaagtgct tcaactgcgg caaggagggc acaccgcca ggaactgccg cgcccccgc    1680 aagaagggct gctggcgctg cggccgcgaa ggacaccaaa tgaaagattg cactgagaga   1740
caggctaatt tcttccgcga ggacctggcc ttcctgcagg gcaaggcccg cgagttcagc   1800
agcgagcaga cccgcgccaa cagccccacc cgccgcgagc tgcaggtgtg gggcggcgag   1860
aacaacagcc tgagcgaggc cggcgccgac cgccagggca ccgtgagctt caacttcccc   1920
cagatcaccc tgtggcagcg ccccctggtg accatcagga tcggcggcca gctcaaggag   1980
gcgctgctcg ccaccggcgc cgacgacacc gtgctggagg agatgaacct gcccggcaag   2040
tggaagccca agatgatcgg cgggatcggg ggcttcatca aggtgcggca gtacgaccag   2100
atccccgtgg agatctgcgg ccacaaggcc atcggcaccg tgctggtggg ccccaccccc   2160
gtgaacatca tcggccgcaa cctgctgacc cagatcggct gcaccctgaa cttccccatc   2220
agccccatcg agacggtgcc cgtgaagctg aagccgggga tggacggccc caaggtcaag   2280
cagtggcccc tgaccgagga aagatcaag gccctggtgg agatctgcac cgagatggag   2340
aaggagggca agatcagcaa gatcggcccc gagaacccct acaacacccc cgtgttcgcc   2400
atcaagaaga aggacagcac caagtggcgc aagctggtgg acttccgcga gctgaacaag   2460
cgcacccagg acttctggga ggtgcagctg ggcatccccc accccgccgg cctgaagaag   2520
aagaagagcg tgaccgtgct ggacgtgggc gacgcctact tcagcgtgcc cctggacaag   2580
gacttccgca gtacaccgc cttcaccatc ccagcatca acaacgagac ccccggcatc   2640
cgctaccagt acaacgtgct gccccagggc tggaagggca gccccgccat cttccagagc   2700
agcatgacca agatcctgga gcccttccgc aagcagaacc ccgacatcgt gatctaccag   2760
gcccccctgt acgtgggcag cgacctggag atcggccagc accgcaccaa gatcgaggag   2820
ctgcgccagc acctgctgcg ctggggcttc accaccccg acaagaagca ccagaaggag   2880 cccccttcc tgcccatcga gctgcacccc gacaagtgga ccgtgcagcc catcatgctg   2940
cccgagaagg acagctggac cgtgaacgac atccagaagc tggtgggcaa gctgaactgg   3000
```

```
                                                            -continued gccagccaga tctacgccgg catcaaggtg aagcagctgt gcaagctgct gcgcggcacc    3060
aaggccctga ccgaggtgat ccccctgacc gaggaggccg agctggagct ggccgagaac    3120
cgcgagatcc tgaaggagcc cgtgcacgag gtgtactacg accccagcaa ggacctggtg    3180
gccgagatcc agaagcaggg ccagggccag tggacctacc agatctacca ggagcccttc    3240
aagaacctga gaccggcaa gtacgcccgc atgcgcggcg cccacaccaa cgacgtgaag    3300
cagctgaccg aggccgtgca aaggtgagc accgagagca tcgtgatctg gggcaagatc    3360
cccaagttca agctgcccat ccagaaggag acctgggagg cctggtggat ggagtactgg    3420
caggccacct ggatccccga gtgggagttc gtgaacaccc ccccctggt gaagctgtgg    3480 taccagctgg agaaggagcc catcgtgggc gccgagacct tctacgtgga cggcgccgcc    3540
aaccgcgaga ccaagctggg caaggccggc tacgtgaccg accggggccg gcagaaggtg    3600
gtgagcatcg ccgacaccac caaccagaag accgagctgc aggccatcca cctggccctg    3660
caggacagcg gcctggaggt gaacatcgtg accgacagcc agtacgccct gggcatcatc    3720
caggcccagc cgacaagag cgagagcgag ctggtgagcc agatcatcga gcagctgatc    3780
aagaaggaga aggtgtacct ggcctgggtg cccgcccaca agggcatcgg cggcaacgag    3840
caggtggaca gctggtgag cgccggcatc cgcaaggtgc tgttcctgaa cggcatcgat    3900
ggcggcatcg tgatctacca gtacatggac gacctgtacg tgggcagcgg cggccctagg    3960
atcgatgagc ccgtgaccc ccgcctggag ccctggaagc accccggcag ccagcccaag    4020
accgccggca ccaactgcta ctgcaagaag tgctgcttcc actgccaggt gagcttcatc    4080
accaagggcc tgggcatcag ctacggccgc aagaagcgcc gccagcgccg ccgcgccccc    4140
cccgacagcg aggtgcacca ggtgagcctg cccaagcagc cgccagcca gccccagggc    4200 gaccccaccg ccccaagga gagcaagaag aaggtggagc gcgagaccga ccgaccccc    4260 gtgcacgaat cgccggccg cagcggcgac agcgacgagg agctgctgca gaccgtgcgc    4320
ttcatcaagt cctgtacca gagcaacccc ctgcccagcc caagggcac cgccaggcc    4380 gacctgaacc gccgccgcg ctggcgcgag cgccagcgcc agatccagag catcagcgcc    4440
tggatcatca gcacccacct gggccgcagc accgagcccg tgcccctgca gctgccccc    4500 gacctgcgcc tgaacctgga ctgcagcgag gactgcggca ccagcggcac ccagggcgtg    4560
ggcagccccc aggtgctggg cgagagcccc gccgtgctgg acagcggcac caaggagctc    4620
gaggccggca agtggagcaa gcgcatgagc ggctggagcc cgtgcgcga gcgcatgaag    4680 cgcgccgagc ccgccgagcc cgccgccgac ggcgtgggcg ccgtgagccg gacctggag    4740 aagcacggcg ccatcaccag cagcaacacc gccgccaaca cgccgactg cgcctggctg    4800 gaggcccagg aggacgagga cgtgggcttc ccgtgcgcc cccaggtgcc cctgcgcccc    4860
atgacctaca aggccgccct ggacctgagc cacttcctga aggagaaggg cggcctggag    4920
ggcctgatct acagccagaa gcgccaggac atcctggacc tgtggatcca ccacacccag    4980
ggctacttcc ccggctggca gaactacacc cccggccccg gcatccgcta ccccctgacc    5040
ttcggctggt gcttcaagct ggtgcccgtg accccgact acgtggagga ggccaacgcc    5100
ggcgagaaca cagcctgct gcaccccatg agccagcacg gcatgacgga ccccgagaag    5160
gaggtgctgg tgtggcgctt cgacagccgc ctggccttcc accacatggc ccgcgagctg    5220
caccccgagt actacaagga ctgcgcttaa gcttcccggg gctagcaccg gttctaga     5278
```

POLYCISTRONIC HIV VECTOR CONSTRUCTS

CROSS-REFERENCE TO RELATED APPLICATIONS

This application claims the benefit of provisional application U.S. Ser. No. 60/568,390, filed May 5, 2004, which application is hereby incorporated by reference in its entirety.

STATEMENT OF FEDERALLY SPONSORED RESEARCH OR DEVELOPMENT

This invention was made, in part, with support from the U.S. Government under contract NIH HIVDDT Contract # N01-AI-05396 awarded by the National Institutes of Health. The Government may have certain rights in this invention.

TECHNICAL FIELD

Polynucleotides encoding HIV polypeptides are described, as are uses of these polynucleotides and polypeptide products including formulations of immunogenic compositions and uses thereof. In particular, polycistronic expression vectors are described.

BACKGROUND

Acquired immune deficiency syndrome (AIDS) is recognized as one of the greatest health threats facing modern medicine. There is, as yet, no cure for this disease.

A great deal of information has been gathered about the HIV, however, to date an effective vaccine has not been identified. Recently, use of polynucleotides encoding antigenic HIV polypeptides in immunogenic compositions has been described. See, e.g., U.S. Pat. No. 5,846,546 to Hurwitz et al.; U.S. Pat. No. 5,840,313 to Vahlne et al.; U.S. Pat. No. 5,876,731 to Sia et al.

Furthermore, U.S. Pat. Nos. 6,689,879; 6,602,705 and International Publications WO 00/39303, WO 00/39302, WO 00/39304, WO 02/04493 describe polynucleotides encoding one or more immunogenic HIV polypeptides that generate humoral and/or cellular responses in vivo.

SUMMARY

Described herein are polynucleotides encoding multiple HIV polypeptides, polypeptides encoded by these sequences, as well as methods of making and using these polynucleotides and/or polypeptides.

In one aspect, the present invention relates to synthetic sequences encoding multiple HIV polypeptides (e.g., sequences encoding HIV Gag, Pol, Tat, Rev and Nef polypeptides). In certain embodiments, the sequences are contained in a vector (e.g., expression cassette) and comprise, in a 5' to 3' orientation, sequences as described herein encoding Tat, Rev, Nef, Gag and Pol. Preferably, the sequences encode single HIV polyprotein. The polypeptides are preferably modified as compared to wild type and may contain one or more mutations that affect one or more functions of the polypeptide. For example, protease activity of the protease region of a Pol polypeptide can be attenuated or inactivated by making the appropriate mutations to the Pol-encoding sequence. Preferably, the sequences described herein encode polypeptides that elicit an immunological response when administered to the subject.

In certain embodiments, the invention relates to a polynucleotide sequence encoding more than one HIV polypeptide, wherein the polynucleotide sequence comprises a sequence having between about 85% to 100% and any integer values therebetween, for example, at least about 85%, preferably about 90%, more preferably about 95%, and more preferably about 98% sequence identity to the sequences or functional fragments thereof taught in the present specification. Further, sequences described herein may also include sequences encoding additional polypeptides, for example, coding sequences for other viral proteins (e.g., hepatitis B or C or other HIV proteins, such as, polynucleotide sequences encoding the same or other HIV polypeptides such as Env, vif, vpr, tat, rev, vpu and nef); cytokines and/or other transgenes. The polynucleotides of the present invention can be produced by recombinant techniques, synthetic techniques, or combinations thereof.

The sequences described herein may be obtained or derived from an HIV strain or subtype. In certain embodiments, the sequences are obtained or derived from a subtype B HIV strain, for example SF2 and/or SF162. In other embodiments, the sequences are obtained or derived from a subtype C HIV strain. Furthermore, one or more of the sequences encoding an HIV polypeptide may be derived from different strains or subtypes.

In another aspect, the present invention relates to generating an immune response in a subject using the sequences (e.g., contained within expression cassettes) of the present invention. The immune responses may be therapeutic and/or prophylactic and may induce cellular and/or humoral (e.g., neutralizing antibody) immune responses against HIV in a subject. In certain embodiments, an immune response is generated by administering one or more sequences as described herein along with one or more polypeptides.

The present invention further includes recombinant expression systems for use in selected host cells, wherein the recombinant expression systems employ one or more of the polynucleotides and expression cassettes of the present invention. In such systems, the polynucleotide sequences are operably linked to control elements compatible with expression in the selected host cell. Numerous expression control elements are known to those in the art, including, but not limited to, the following: transcription promoters, transcription enhancer elements, transcription termination signals, polyadenylation sequences, sequences for optimization of initiation of translation, and translation termination sequences. Exemplary transcription promoters include, but are not limited to those derived from CMV, CMV+intron A, SV40, RSV, HIV-Ltr, MMLV-ltr, and metallothionein.

In another aspect the invention includes cells comprising one or more of the sequences of the present invention where the polynucleotide sequences are operably linked to control elements compatible with expression in the selected cell. In one embodiment such cells are mammalian cells. Exemplary mammalian cells include, but are not limited to, BHK, VERO, HT1080, 293, RD, COS-7, and CHO cells. Other cells, cell types, tissue types, etc., that may be useful in the practice of the present invention include, but are not limited to, those obtained from the following: insects (e.g., *Trichoplusia ni* (Tn5) and Sf9), avian (e.g., hens' cells such as hens' embryo cells (CEF cells)), bacteria, yeast, plants, antigen presenting cells (e.g., macrophage, monocytes, dendritic cells, B-cells, T-cells, stem cells, and progenitor cells thereof), primary cells, immortalized cells, tumor-derived cells.

In another aspect, the present invention includes compositions for generating an immunological response, where the composition typically comprises at least one of the expression cassettes of the present invention and may, for example, contain combinations of expression cassettes such as one or more expression cassettes. Such compositions may further contain an adjuvant or adjuvants. The compositions may also contain one or more HIV polypeptides. The HIV polypeptides may correspond to the polypeptides encoded by the expression cassette(s) in the composition, or may be different from those encoded by the expression cassettes. In compositions containing both expression cassettes (or polynucleotides of the present invention) and polypeptides, various expression cassettes of the present invention can be mixed and/or matched with various HIV polypeptides described herein.

In another aspect the present invention includes methods of immunization of a subject. In the method any of the above-described compositions are into the subject under conditions that are compatible with expression of the expression cassette(s) in the subject. In one embodiment, the expression cassettes (or polynucleotides of the present invention) can be introduced using a gene delivery vector. The gene delivery vector can, for example, be a non-viral vector or a viral vector. Exemplary viral vectors include, but are not limited to eukaryotic layered vector initiation systems, Sindbis-virus (or other alphavirus) derived vectors, retroviral vectors, and lentiviral vectors. Other exemplary vectors include, but are not limited to, pCMVKm2, pCMV6a, pCMV-link, and pCMVPLEdhfr. Compositions useful for generating an immunological response can also be delivered using a particulate carrier (e.g., PLG or CTAB-PLG microparticles). Further, such compositions can be coated on, for example, gold or tungsten particles and the coated particles delivered to the subject using, for example, a gene gun. The compositions can also be formulated as liposomes. In one embodiment of this method, the subject is a mammal and can, for example, be a human.

The polynucleotides of the present invention may be employed singly or in combination.

These and other embodiments of the present invention will readily occur to those of ordinary skill in the art in view of the disclosure herein.

BRIEF DESCRIPTION OF THE FIGURES

FIGS. 1A to 1B depict the nucleotide sequence of a construct designated TRNgagCpolIna (SEQ ID NO:1). The construct includes synthetic sequences encoding an HIV polyprotein including HIV Tat, Rev, Nef, Gag and Pol polypeptides. The protease function of Pol has been inactivated. The sequences encoding the HIV polyprotein are ordered, in a 5' to 3' direction, Tat-, Rev-, Nef-, Gag-, Pol- encoding sequences. In addition, the construct includes HIV protease cleavage sites (ATIM/MQR) encoded by residues 1294 to 1314, 2443 to 2463, and 2878 to 2898 of FIG. 1A.

FIGS. 2A to 2B depict the nucleotide sequence of a construct designated gagCpolInaTRN (SEQ ID NO:2). The construct includes synthetic sequences encoding an HIV polyprotein including HIV Gag, Pol, Tat, Rev, Nef, polypeptides. The protease function of Pol has been inactivated. The sequences encoding the HIV polyprotein are ordered, in a 5' to 3' direction, Gag-, Pol-, Tat-, Rev-, Nef-encoding sequences. In addition, the construct includes HIV protease cleavage sites (ATIM/MQR) encoded by residues 1,138 to 1,158 and 1,573 to 1,593.

DETAILED DESCRIPTION

Figure 3:
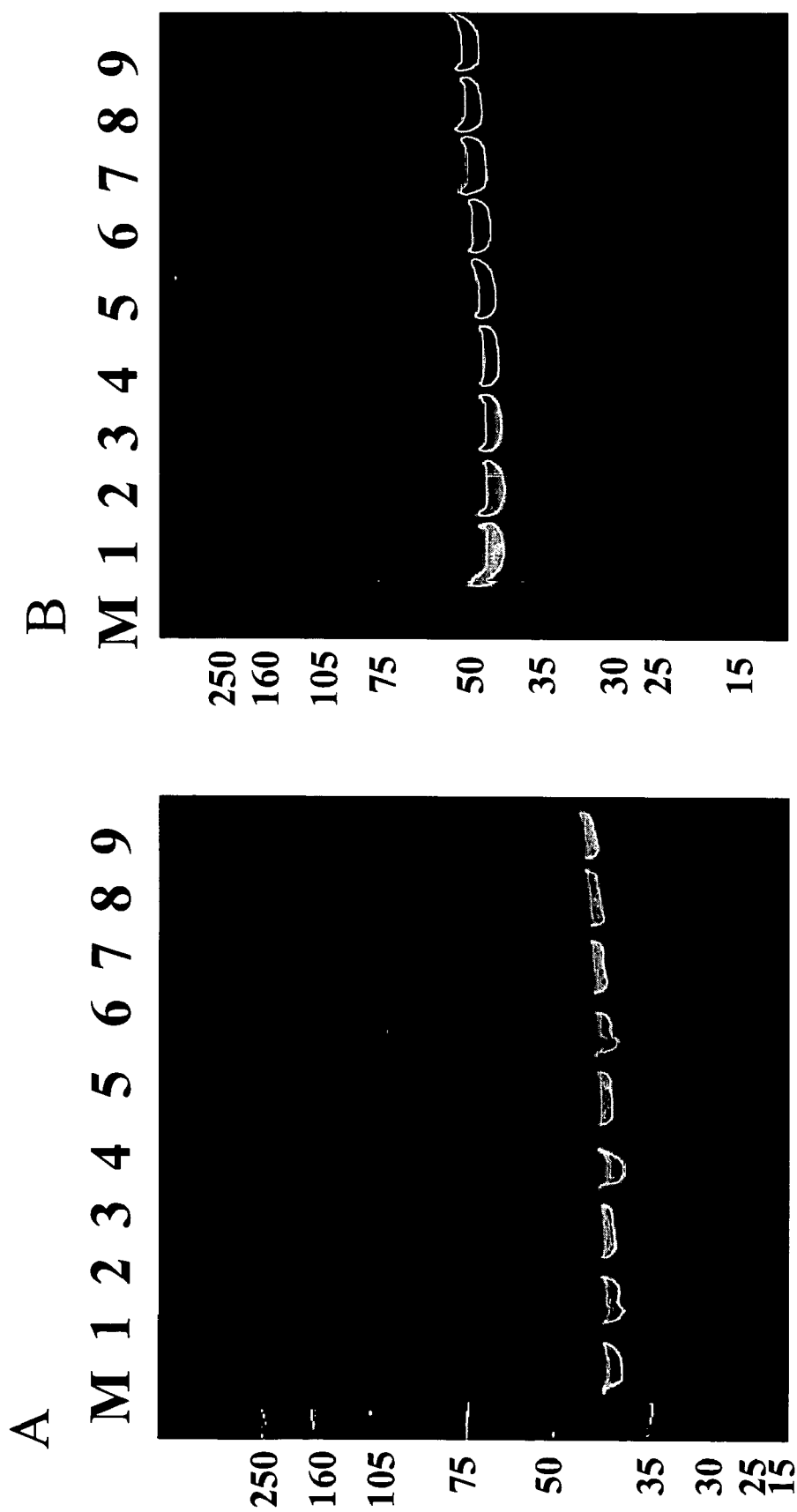
FIG. 3, panels A and B, are reproductions of gels showing Western Blot analysis of protein levels in lysate of cells transfected with various HIV polypeptide-encoding constructs. Panel A depicts results obtained 48 hours post-transfection. Panel B depicts results obtained 72 hours post-transfection. In both panels, the lane designated "M" shows the marker. Lane 1 is shows protein levels in cells transfected with constructs encoding Gag. Lane 2 shows protein levels in cells transfected with constructs encoding Gag and Pol. The protease function of Pol has been inactivated. Lane 3 shows protein levels in cells transfected with constructs comprising, in 5' to 3' orientation, sequences encoding, Gag, Pol (inactivated), Tat, Rev and Nef. Lane 4 shows protein levels in lysates of cells transfected with constructs comprising, in a 5' to 3' orientation, sequences encoding, Tat, Rev, Nef, Gag, and inactivated Pol. Lane 5 shows protein levels in cells transfected with constructs encoding Gag and Pol. The protease function of Pol has been attenuated. Lane 6 shows protein levels in cells transfected with constructs comprising, in 5' to 3' orientation, sequences encoding, Gag, Pol (attenuated), Tat, Rev and Nef. Lane 7 shows protein levels in lysates of cells transfected with constructs comprising, in a 5' to 3' orientation, sequences encoding, Tat, Rev, Nef, Gag, and attenuated Pol. Lane 8 shows protein levels from cells transfected with a construct encoding p2Pol. Lane 9 is a mock lysate control.

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences,* 18th Edition (Easton, Pa.: Mack Publishing Company, 1990); *Methods In Enzymology* (S. Colowick and N. Kaplan, eds., Academic Press, Inc.); and *Handbook of Experimental Immunology,* Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Short Protocols in Molecular Biology,* 4th ed. (Ausubel et al. eds., 1999, John Wiley & Sons); *Molecular Biology Techniques: An Intensive Laboratory Course,* (Ream et al., eds., 1998, Academic Press); *PCR (Introduction to Biotechniques Series),* 2nd ed. (Newton & Graham eds., 1997, Springer Verlag).

All publications, patents and patent applications cited herein, whether supra or infra, are hereby incorporated by reference in their entirety.

As used in this specification, the singular forms "a," "an" and "the" include plural references unless the content clearly dictates otherwise. Thus, for example, reference to "an antigen" includes a mixture of two or more such agents.

1. Definitions

In describing the present invention, the following terms will be employed, and are intended to be defined as indicated below.

"Synthetic" sequences, as used herein, refers to HIV polypeptide-encoding polynucleotides whose expression has been modified as described herein, for example, by codon substitution, altered activities, and/or inactivation of inhibitory sequences. "Wild-type" or "native" sequences, as used herein, refers to polypeptide encoding sequences that are essentially as they are found in nature, e.g., Gag, Pol, Vif, Vpr, Tat, Rev, Vpu, Env and/or Nef encoding sequences as found in HIV isolates, e.g., SF162, SF2, AF110965, AF110967, AF110968, AF110975, 8_5_TV1_C.ZA, 8_2_TV1_C.ZA or 12-5_1_TV2_C.ZA.

Thus, the term "Pol" refers to one or more of the following polypeptides: polymerase (p6Pol); protease (prot); reverse transcriptase (p66RT or RT); RNAseH (p15RNAseH); and/or integrase (p31Int or Int). Identification of gene regions for any selected HIV isolate can be performed by one of ordinary skill in the art based on the teachings presented herein and the information known in the art, for example, by performing alignments relative to other known HIV isolates, for example, Subtype B isolates with gene regions (e.g., SF2, GenBank Accession number K02007; SF162, GenBank Accession Number M38428, both herein incorporated by reference) and Subtype C isolates with gene regions (e.g., GenBank Accession Number AF110965 and GenBank Accession Number AF110975, both herein incorporated by reference).

The term "HIV polypeptide" refers to any amino acid sequence that exhibits sequence homology to native HIV polypeptides (e.g., Gag, Env, Prot, Pol, RT, Int, vif, vpr, vpu, tat, rev, nef and/or combinations thereof) and/or which is functional. Non-limiting examples of functions that may be exhibited by HIV polypeptides include, use as immunogens (e.g., to generate a humoral and/or cellular immune response, including immune responses that are specific to the HIV polypeptide(s)), use in diagnostics (e.g., bound by suitable antibodies for use in ELISAs or other immunoassays) and/or polypeptides which exhibit one or more biological activities associated with the wild type or synthetic HIV polypeptide. For example, as used herein, the term "Gag polypeptide" may refer to a polypeptide that is bound by one or more anti-Gag antibodies; elicits a humoral and/or cellular immune response; and/or exhibits the ability to form particles.

An "antigen" refers to a molecule containing one or more epitopes (either linear, conformational or both) that will stimulate a host's immune system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide that expresses an antigen or antigenic determinant in vivo, such as in gene therapy and DNA immunization applications, is also included in the definition of antigen herein.

For purposes of the present invention, immunogens can be derived from any of several known viruses, bacteria, parasites and fungi, as described more fully below, for example immunogens derived from an HIV. Furthermore, for purposes of the present invention, an "immunogen" refers to a protein that includes modifications, such as deletions, additions and substitutions (generally conservative in nature), to the native sequence, so long as the protein maintains the ability to elicit an immunological response, as defined herein. These modifications may be deliberate, as through site-directed mutagenesis, or may be accidental, such as through mutations of hosts that produce the antigens. By "immunogenic fragment" is meant a fragment of an HIV polypeptide that includes one or more epitopes and thus elicits one or more of the immunological responses described herein. Such fragments can be identified by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715, all incorporated herein by reference in their entireties.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular immunogen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., J. Immunol. (1993) 151:4189-4199; Doe et al., Eur. J. Immunol. (1994) 24:2369-2376. Recent methods of measuring cell-mediated immune response include measurement of intracellular cytokines or cytokine secretion by T-cell populations, or by measurement of epitope specific T-cells (e.g., by the tetramer technique)(reviewed by McMichael, A. J., and O'Callaghan, C. A., J. Exp. Med. 187(9)1367-1371, 1998; Mcheyzer-Williams, M. G., et al, Immunol. Rev. 150:5-21, 1996; Lalvani, A., et al, J. Exp. Med. 186:859-865, 1997).

Thus, an immunological response as used herein may be one that stimulates the production of antibodies (e.g., neutralizing antibodies that block bacterial toxins and pathogens such as viruses entering cells and replicating by binding to toxins and pathogens, typically protecting cells from infection and destruction). The antigen of interest may also elicit production of CTLs. Hence, an immunological response may include one or more of the following effects: the production of antibodies by B-cells; and/or the activation of suppressor T-cells and/or δγ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art. (See, e.g., Montefiori et al. (1988) *J. Clin Microbiol.* 26:231-235; Dreyer et al. (1999) *AIDS Res Hum Retroviruses* (1999) 15(17):1563-1571).

An "immunogenic composition" is a composition that comprises an antigenic molecule where administration of the composition to a subject results in the development in the subject of a humoral and/or a cellular immune response to the antigenic molecule of interest. The immunogenic composition can be introduced directly into a recipient subject, such as by injection, inhalation, oral, intranasal and mucosal (e.g., intra-rectally or intra-vaginally) administration.

By "subunit vaccine" is meant a vaccine composition that includes one or more selected antigens but not all antigens, derived from or homologous to, an antigen from a pathogen of interest such as from a virus, bacterium, parasite or fungus. Such a composition is substantially free of intact pathogen cells or pathogenic particles, or the lysate of such cells or particles. Thus, a "subunit vaccine" can be prepared from at least partially purified (preferably substantially purified) immunogenic polypeptides from the pathogen, or analogs thereof. The method of obtaining an antigen included in the subunit vaccine can thus include standard purification techniques, recombinant production, or synthetic production.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

A "coding sequence" or a sequence that "encodes" a selected polypeptide is a nucleic acid molecule that is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence such as a stop codon may be located 3' to the coding sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

A "polynucleotide coding sequence" or a sequence that "encodes" a selected polypeptide, is a nucleic acid molecule that is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. Exemplary coding sequences are the modified viral polypeptide-coding sequences of the present invention. A transcription termination sequence may be located 3' to the coding sequence. Typical "control elements", include, but are not limited to, transcription regulators, such as promoters, transcription enhancer elements, transcription termination signals, and polyadenylation sequences; and translation regulators, such as sequences for optimization of initiation of translation, e.g., Shine-Dalgarno (ribosome binding site) sequences, Kozak sequences (i.e., sequences for the optimization of translation, located, for example, 5' to the coding sequence), leader sequences (heterologous or native), translation initiation codon (e.g., ATG), and translation termination sequences. In certain embodiments, one or more translation regulation or initiation sequences (e.g., the leader sequence) are derived from wild-type translation initiation sequences, i.e., sequences that regulate translation of the coding region in their native state. Wild-type leader sequences that have been modified, using the methods described herein, also find use in the present invention. Native or modified leader sequences can be from any source, for example other strains, variants and/or subtypes of HIV or non-HIV sources (e.g., tpa leader sequence exemplified herein). Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

A "nucleic acid" molecule can include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, cl. Acids Res. 14(6):6745-6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: ncbi.nlm.gov/cgi-bin/BLAST.

One of skill in the art can readily determine the proper search parameters to use for a given sequence, exemplary preferred Smith Waterman based parameters are presented above. For example, the search parameters may vary based on the size of the sequence in question. Thus, for the polynucleotide sequences of the present invention the length of the polynucleotide sequence disclosed herein is searched against a selected database and compared to sequences of essentially the same length to determine percent identity. For example, a representative embodiment of the present invention would include an isolated polynucleotide having X contiguous nucleotides, wherein (i) the X contiguous nucleotides have at least about a selected level of percent identity relative to Y contiguous nucleotides of the sequences described herein, and (ii) for search purposes X equals Y, wherein Y is a selected reference polynucleotide of defined length.

The sequences of the present invention can include fragments of the sequences, for example, from about 15 nucleotides up to the number of nucleotides present in the full-length sequences described herein (e.g., see the Sequence Listing, Figures, and claims), including all integer values falling within the above-described range. For example, fragments of the polynucleotide sequences of the present invention may be 30-60 nucleotides, 60-120 nucleotides, 120-240 nucleotides, 240-480 nucleotides, 480-1000 nucleotides, and all integer values therebetween.

The synthetic polynucleotides of the present invention include related polynucleotide sequences having about 80% to 100%, greater than 80-85%, preferably greater than 90-92%, more preferably greater than 92-95%, more preferably greater than 95%, and most preferably greater than 98% up to 100% (including all integer values falling within these described ranges) sequence identity to the synthetic polynucleotide sequences disclosed herein (for example, to the claimed sequences or other sequences of the present invention) when the sequences of the present invention are used as the query sequence against, for example, a database of sequences.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., supra or Ausubel et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, Nucleic Acid Hybridization: A Practical Approach, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., supra or Ausubel et al., supra).

A first polynucleotide is "derived from" second polynucleotide if it has the same or substantially the same basepair sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

Generally, a viral polypeptide is "derived from" a particular polypeptide of a virus (viral polypeptide) if it is (i) encoded by an open reading frame of a polynucleotide of that virus (viral polynucleotide), or (ii) displays sequence identity to polypeptides of that virus as described above.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences that are immunologically identifiable with a polypeptide encoded by the sequence. Further, polyproteins can be constructed by fusing in-frame two or more polynucleotide sequences encoding polypeptide or peptide products. Further, polycistronic coding sequences may be produced by placing two or more polynucleotide sequences encoding polypeptide products adjacent each other, typically under the control of one promoter, wherein each polypeptide coding sequence may be modified to include sequences for internal ribosome binding sites.

"Purified polynucleotide" refers to a polynucleotide of interest or fragment thereof that is essentially free, e.g., contains less than about 50%, preferably less than about 70%, and more preferably less than about 90%, of the protein with which the polynucleotide is naturally associated. Techniques for purifying polynucleotides of interest are well known in the art and include, for example, disruption of the cell containing the polynucleotide with a chaotropic agent and separation of the polynucleotide(s) and proteins by ion-exchange chromatography, affinity chromatography and sedimentation according to density.

By "nucleic acid immunization" is meant the introduction of a nucleic acid molecule encoding one or more selected antigens into a host cell, for the in vivo expression of an antigen, antigens, an epitope, or epitopes. The nucleic acid molecule can be introduced directly into a recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

"Gene transfer" or "gene delivery" refers to methods or systems for reliably inserting DNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from alphaviruses, pox viruses and vaccinia viruses. When used for immunization, such gene delivery expression vectors may be referred to as vaccines or vaccine vectors.

"T lymphocytes" or "T cells" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring gene sequences to target cells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors.

Transfer of a "suicide gene" (e.g., a drug-susceptibility gene) to a target cell renders the cell sensitive to compounds or compositions that are relatively nontoxic to normal cells. Moolten, F. L. (1994) Cancer Gene Ther. 1:279-287. Examples of suicide genes are thymidine kinase of herpes simplex virus (HSV-tk), cytochrome P450 (Manome et al. (1996) Gene Therapy 3:513-520), human deoxycytidine kinase (Manome et al. (1996) Nature Medicine 2(5):567-573) and the bacterial enzyme cytosine deaminase (Dong et al. (1996) Human Gene Therapy 7:713-720). Cells that express these genes are rendered sensitive to the effects of the relatively nontoxic prodrugs ganciclovir (HSV-tk), cyclophosphamide (cytochrome P450 2B1), cytosine arabinoside (human deoxycytidine kinase) or 5-fluorocytosine (bacterial cytosine deaminase). Culver et al. (1992) Science 256:1550-1552, Huber et al. (1994) Proc. Natl. Acad. Sci. USA 91:8302-8306.

A "selectable marker" or "reporter marker" refers to a nucleotide sequence included in a gene transfer vector that has no therapeutic activity, but rather is included to allow for simpler preparation, manufacturing, characterization or testing of the gene transfer vector.

A "specific binding agent" refers to a member of a specific binding pair of molecules wherein one of the molecules specifically binds to the second molecule through chemical and/or physical means. One example of a specific binding agent is an antibody directed against a selected antigen.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, "treatment" refers to any of (I) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

By "co-administration" is meant administration of more than one composition or molecule. Thus, co-administration includes concurrent administration or sequentially administration (in any order), via the same or different routes of administration. Non-limiting examples of co-administration regimes include, co-administration of nucleic acid and polypeptide; co-administration of different nucleic acids (e.g., different expression cassettes as described herein and/or different gene delivery vectors); and co-administration of different polypeptides (e.g., different HIV polypeptides and/or different adjuvants). The term also encompasses multiple administrations of one of the co-administered molecules or compositions (e.g., multiple administrations of one or more of the polynucleotides and/or expression cassettes described herein followed by one or more administrations of a polypeptide-containing composition). In cases where the molecules or compositions are delivered sequentially, the time between each administration can be readily determined by one of skill in the art in view of the teachings herein.

"Lentiviral vector", and "recombinant lentiviral vector" refer to a nucleic acid construct that carries, and within certain embodiments, is capable of directing the expression of a nucleic acid molecule of interest. The lentiviral vector include at least one transcriptional promoter/enhancer or locus defining element(s), or other elements which control gene expression by other means such as alternate splicing, nuclear RNA export, post-translational modification of messenger, or post-transcriptional modification of protein. Such vector constructs must also include a packaging signal, long terminal repeats (LTRS) or portion thereof, and positive and negative strand primer binding sites appropriate to the retrovirus used (if these are not already present in the retroviral vector). Optionally, the recombinant lentiviral vector may also include a signal that directs polyadenylation, selectable markers such as Neo, TK, hygromycin, phleomycin, histidinol, or DHFR, as well as one or more restriction sites and a translation termination sequence. By way of example, such vectors typically include a 5' LTR, a tRNA binding site, a packaging signal, an origin of second strand DNA synthesis, and a 3'LTR or a portion thereof "Lentiviral vector particle" as utilized within the present invention refers to a lentivirus that carries at least one gene of interest. The retrovirus may also contain a selectable marker. The recombinant lentivirus is capable of reverse transcribing its genetic material (RNA) into DNA and incorporating this genetic material into a host cell's DNA upon infection. Lentiviral vector particles may have a lentiviral envelope, a non-lentiviral envelope (e.g., an ampho or VSV-G envelope), or a chimeric envelope. An "alphavirus vector" refers to a nucleic acid construct that carries, and within certain embodiments, is capable of directing the expression of a nucleic acid molecule of interest. Alphavirus vectors may be utilized in several formats, including DNA, RNA, and recombinant replicon particles. Such replicon vectors have been derived from alphaviruses that include, for example, Sindbis virus, Semliki Forest virus, and/or Venezuelan equine encephalitis virus. See, e.g., U.S. Pat. Nos. 5,789,245; 5,814,482; and 6,376,235 and WO 02/099035. Chimeric alphavirus vectors are described, for example, in U.S. patent Publications 20030232324 and 20030148262. The terms "alphavirus RNA replicon vector", "RNA replicon vector", "replicon vector" or "replicon" refer to an RNA molecule that is capable of directing its own amplification or self-replication in vivo, within a target cell. To direct its own amplification, the RNA molecule should encode the polymerase(s) necessary to catalyze RNA amplification (e.g., alphavirus nonstructural proteins nsP1, nsP2, nsP3, nsP4) and also contain cis RNA sequences required for replication which are recognized and utilized by the encoded polymerase(s). An alphavirus RNA vector replicon typically contains following ordered elements: 5' viral or cellular sequences required for nonstructural protein-mediated amplification (may also be referred to as 5' CSE, or 5' cis replication sequence, or 5' viral sequences required in cis for replication, or 5' sequence which is capable of initiating transcription of an alphavirus), sequences which, when expressed, code for biologically active alphavirus nonstructural proteins (e.g., nsP1, nsP2, nsP3, nsP4), and 3' viral or cellular sequences required for nonstructural protein-mediated amplification (may also be referred as 3' CSE, or 3' viral sequences required in cis for replication, or an alphavirus RNA polymerase recognition sequence). The alphavirus RNA vector replicon also should contain a means to express one or more heterologous sequence(s), such as for example, an IRES or a viral (e.g., alphaviral) subgenomic promoter (e.g., junction region promoter) which may, in certain embodiments, be modified in order to increase or reduce viral transcription of the subgenomic fragment, or to decrease homology with defective helper or structural protein expression cassettes, and one or more heterologous sequence(s) to be expressed. When used as vectors, the replicons will also contain additional sequences, for example, one or more heterologous sequence(s) encoding one or more polypeptides (e.g., a protein-encoding gene or a 3' proximal gene) and/or a polyadenylate tract.

"Nucleic acid expression vector" or "Expression cassette" refers to an assembly that is capable of directing the expression of a sequence or gene of interest. The nucleic acid expression vector typically includes a promoter that is operably linked to the sequences or gene(s) of interest. Other control elements may be present as well. Expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

"Packaging cell" refers to a cell that contains those elements necessary for production of infectious recombinant viral that are lacking in a recombinant viral vector. Typically, such packaging cells contain one or more expression cassettes that are capable of expressing proteins encoded by the sequences described herein.

"Producer cell" or "vector producing cell" refers to a cell that contains all elements necessary for production of recombinant viral vector particles.

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2. General Overview

Numerous studies conducted in humans and animals have clearly demonstrated that, in order to be effective, HIV vaccines must include sufficient amounts of HIV proteins. Typically, the levels of expression required for a robust immune response are higher than those produced from wild-type sequences. Consequently, we have previously developed constructs in which the sequences are modified to improve expression over wild type and provide robust immune responses. See, e.g., U.S. Pat. No. 6,602,705; and International Publications WO 02/00250; WO 02/04493; WO 03/004620; WO 03/004657; and WO 03/020876.

Described herein are sequences that express HIV proteins at higher levels than wild type sequences. High levels of protein expression are a desirable starting point for the development of immunogenic compositions. In particular, polycistronic vectors comprising sequences encoding various HIV polypeptides as a single polyprotein are described, wherein expression of the HIV polypeptides is improved as compared to wild type.

3. The HIV Genome

The HIV genome and various polypeptide-encoding regions are known. For example, GenBank Accession No. K02007 describes various regions of $HIV_{SF2}$ ("SF2"). It will be readily apparent to one of ordinary skill in the art in view of the teachings of the present disclosure how to determine corresponding regions in other HIV strains or variants (e.g., isolates $HIV_{IIIb}$, $HIV\text{-}1_{SF162}$, $HIV\text{-}1_{SF170}$, $HIV_{LAV}$, $HIV_{LAI}$, $HIV_{MN}$, $HIV\text{-}1_{CM235}$, $HIV\text{-}1_{US4}$, other HIV-1 strains from diverse subtypes(e.g., subtypes, A through G, and O), HIV-2 strains and diverse subtypes (e.g., $HIV\text{-}2_{UC1}$ and $HIV\text{-}2_{UC2}$), and simian immunodeficiency virus (SIV). (See, e.g., Virology, 3rd Edition (W. K. Joklik ed. 1988); Fundamental Virology, 2nd Edition (B. N. Fields and D. M. Knipe, eds. 1991); Virology, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify the various regions).

4. Synthetic Sequences

One aspect of the present invention is the generation of synthetic sequences (modified as compared to wild type) encoding HIV-1 polypeptides, and related sequences. When incorporated into an expression vector, the sequences exhibit improved expression relative to the corresponding wild-type sequences. In addition, when the sequences incorporated into the vector are ordered such that Gag- and Pol-encoding sequences are 3' to sequences encoding Tat, Rev and Nef, expression in both lysate and supernatant is further improved as compared to individual synthetic sequences and to synthetic sequences ordered with Tat, Rev and Nef sequences 3' to Gag and Pol.

The sequences described herein were prepared essentially as described in U.S. Pat. No. 6,602,705. Briefly, HIV-1 codon usage pattern was modified so that the resulting nucleic acid coding sequence was comparable to codon usage found in highly expressed human genes. In addition, inhibitory (or instability) elements (INS) located within the coding sequences of, for example, the Gag and/or protease coding sequences were inactivated or attenuated, for example by introducing multiple point mutations that did not alter the reading frame of the encoded proteins. Furthermore, for some genes the coding sequence has been altered such that the polynucleotide coding sequence encodes a gene product that is inactive or non-functional (e.g., inactivated polymerase, protease, tat, rev, nef, vif, vpr, and/or vpu gene products). Example 1 describes some exemplary mutations.

Synthetic expression cassettes, derived from HIV Type B coding sequences, exemplified herein include, but are not limited to, those shown in FIGS. 1 and 2. "Gag-complete" or "Gagc" refers to in-frame polyproteins comprising, e.g., Gag and pol, wherein the p6 portion of Gag is present.

Additional polynucleotide sequences that may be employed in some aspects of the present invention have been described in U.S. Pat. Nos. 6,689,879; 6,602,705; WO 00/39302, WO 00/39303, WO 00/39304, and WO 02/04493, all of which are herein incorporated by reference in their entireties.

Further, the synthetic sequences of the present invention include related polynucleotide sequences having greater than 85%, preferably greater than 90%, more preferably greater than 95%, and most preferably greater than 98% sequence identity to the synthetic polynucleotide sequences disclosed herein. Sequences exhibiting the requisite homology may be generated, for example, by gene shuffling techniques as described for example in U.S. Pat. Nos. 6,323,030; 6,444,468; 6,420,175; and 6,413,774, incorporated herein in their entireties by reference.

The synthetic coding sequences are assembled by methods known in the art, for example by companies such as the Midland Certified Reagent Company (Midland, Tex.).

As noted above, the synthetic sequences described herein are modified from wild type codon usage to codon usage more typical in humans. Additional modifications include, but are not limited to, addition of cleavage sites, leader sequences or the like; addition of other sequences (HIV or non-HIV) and/or introduction of mutations into one or more of the sequences such that non-functional variants were created.

For instance, the protease activity of Pol is preferably attenuated or inactivated. In other embodiments, the integrase and/or RNase H activity of Pol is attenuated or inactivated. Table A sets forth exemplary mutations affecting the activity of several HIV genes. All references cited are herein incorporated by reference.

TABLE A

| Gene | "Region" | Exemplary Mutations |
|---|---|---|
| Pol | prot | Att = Reduced activity by attenuation of Protease (Thr26Ser) (e.g., Konvalinka et al., 1995, J Virol 69: 7180-86) |
|  |  | Ina = Mutated Protease, nonfunctional enzyme (Asp25Ala)(e.g., Konvalinka et al., 1995, J Virol 69: 7180-86) |
|  | RT | YM = Deletion of catalytic center (YMDD__AP) (e.g., Biochemistry, 1995, 34, 5351, Patel et. al.) |
|  |  | WM = Deletion of primer grip region (WMGY__PI) (e.g., J Biol Chem, 272, 17, 11157, Palaniappan, et. al., 1997) |
|  | RNase | no direct mutations, RnaseH is affected by "WM" mutation in RT |
|  | Integrase | 1) Mutation of HHCC domain, Cys40Ala (e.g., Wiskerchen et. al., 1995, J Virol, 69: 376). |
|  |  | 2.) Inactivation catalytic center, Asp64Ala, Asp116Ala, Glu152Ala (e.g., Wiskerchen et. al., 1995, J Virol, 69: 376). |
|  |  | 3) Inactivation of minimal DNA binding domain (MDBD), deletion of Trp235(e.g., Ishikawa et. al., 1999, J Virol, 73: 4475). Constructs int.opt.mut.SF2 and int.opt.mut__C (South Africa TV1) both contain all these mutations (1, 2, and 3) |
| Tat |  | Mutants of Tat in transactivation domain (e.g., Caputo et al., 1996, Gene Ther. 3: 235) |
|  |  | cys22 mutant (Cys22Gly) = TatC22 |
|  |  | cys37 mutant (Cys37Ser) = TatC37 |
|  |  | cys22/37 double mutant = TatC22/37 |
| Rev |  | Mutations in Rev domains (e.g., Thomas et al., 1998, J Virol. 72: 2935-44) |
|  |  | Mutation in RNA binding-nuclear localization ArgArg38, 39AspLeu = M5 |
|  |  | Mutation in activation domain LeuGlu78, 79AspLeu = M10 |
| Nef |  | Mutations of myristoyilation signal and in oligomerization domain: |
|  |  | 1. Single point mutation myristoyilation signal: Gly-to-Ala = -Myr |
|  |  | 2. Deletion of N-terminal first 18 (sub-type B, e.g., SF162) or 19 (sub-type C, e.g., South Africa clones) amino acids: -Myr18 or -Myr19 (respectively) |
|  |  | (e.g., Peng and Robert-Guroff, 2001, Immunol Letters 78: 195-200) |
|  |  | Single point mutation oligomerization: |

TABLE A-continued

| Gene | "Region" | Exemplary Mutations |
|---|---|---|
| | | (e.g., Liu et al., 2000, J Virol 74: 5310-19) Asp125Gly (sub B SF162) or Asp124Gly (sub C South Africa clones) Mutations affecting (1) infectivity (replication) of HIV-virions and/or (2) CD4 down regulation, (e.g., Lundquist et al. (2002) J Virol. 76(9): 4625-33) |

The sequences may include a sequence that encodes the first 6 amino acids of the integrase polypeptide. This 6 amino acid region is believed to provide a cleavage recognition site recognized by HIV protease (see, e.g., McComack et al. (1997) FEBS Letts 414:84-88). Constructs may include a multiple cloning site (MCS) for insertion of one or more transgenes, typically at the 3' end of the construct. In addition, a cassette encoding a catalytic center epitope derived from the catalytic center in RT is typically included 3' of the sequence encoding 6 amino acids of integrase. This cassette encodes Ile178 through Serine 191 of RT and may be added to keep this well conserved region as a possible CTL epitope. Further, the constructs contain an insertion mutations to preserve the reading frame. (see, e.g., Park et al. (1991) J. Virol. 65:5111).

The HIV polypeptide-encoding expression cassettes described herein may also contain one or more further sequences encoding, for example, one or more transgenes. Further sequences (e.g., transgenes) useful in the practice of the present invention include, but are not limited to, further sequences encoding further viral epitopes/antigens, including but not limited to, HIV antigens (e.g., derived from one or more HIV isolate, including HIV-1 or HIV-2 strain antigens, such as gag (p24gag and p55gag), env (gp160 and gp41), pol, tat, nef, rev, vpu, miniproteins, (preferably p55 gag and gp140v delete) and antigens from the isolates $HIV_{IIIB}$, $HIV_{SF2}$, $HIV_{LAV}$, $HIV_{LAI}$, $HIV_{MN}$, $HIV-1_{CM235}$, $HIV-1_{US4}$, HIV-2; simian immunodeficiency virus (SIV) among others;

Hepatitis A virus, such as inactivated virus;

Hepatitis B virus (HBV) antigens, such as the surface and/or core antigens (sAg), as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, (see, e.g., "HBV Vaccines—Human Vaccines and Vaccination, pp. 159-176; and U.S. Pat. Nos. 4,722,840, 5,098,704, 5,324,513; Beames et al., J. Virol. (1995) 69:6833-6838, Birnbaum et al., J. Virol. (1990) 64:3319-3330; and Zhou et al., J. Virol. (1991) 65:5457-5464);

Hepatitis C virus (HCV) antigens (e.g., E1, E2, E1/E2; see, Houghton et al., Hepatology (1991); Houghton, M., et al., U.S. Pat. No. 5,714,596, issued Feb. 3, 1998; Houghton, M., et al., U.S. Pat. No. 5,712,088, issued Jan. 27, 1998; Houghton, M., et al., U.S. Pat. No. 5,683,864, issued Nov. 4, 1997; Weiner, A. J., et al., U.S. Pat. No. 5,728,520, issued Mar. 17, 1998; Weiner, A. J., et al., U.S. Pat. No. 5,766,845, issued Jun. 16, 1998; Weiner, A. J., et al., U.S. Pat. No. 5,670,152, issued Sep. 23, 1997; all herein incorporated by reference; NS345 polyprotein, NS 345-core polyprotein, core, and/or peptides from the nonstructural regions (WO 89/04669; WO 90/11089; and WO 90/14436);

Delta hepatitis virus (HDV) antigens, particularly δ-antigen from HDV (see, e.g., U.S. Pat. No. 5,378,814);

Hepatitis E virus (HE V) antigens;

Hepatitis G virus (HGV) antigens;

Varcicella zoster virus antigens, particularly antigens derived from varicella zoster virus (VZV) (J. Gen. Virol. (1986) 67:1759);

Epstein-Barr virus antigens, particularly antigens derived from EBV (Baer et al., Nature (1984) 310:207);

Cytomegalovirus (CMV) antigens, including gB and gH (Cytomegaloviruses (J. K. McDougall, ed., Springer-Verlag 1990) pp. 125-169);

Herpes simplex virus antigens including antigens from HSV-1 or HSV-2 strains and glycoproteins gB, gD and gH (McGeoch et al., J. Gen. Virol. (1988) 69:1531 and U.S. Pat. No. 5,171,568);

Human Herpes Virus antigens, such as antigens derived from other human herpesviruses such as HHV6 and HHV7; and HPV antigens, including antigens associated with or derived from human papillomavirus (HPV), for example, one or more of E1-E7, L1, L2, and fusions thereof, particularly the compositions of the invention may include a virus-like particle (VLP) comprising the L1 major capsid protein, more particular still, the HPV antigens are protective against one or more of HPV serotypes 6, 11, 16 and/or 18;

Influenza, including whole viral particles (attenuated), split, or subunit comprising hemagglutinin (HA) and/or neuraminidase (NA) surface proteins, the influenza antigens may be derived from chicken embryos or propogated on cell culture, and/or the influenza antigens are derived from influenza type A, B, and/or C, among others;

Respiratory syncytial virus (RSV) antigens including the F protein of the A2 strain of RSV (J Gen Virol. November 2004; 85(Pt 11):3229) and/or G glycoprotein;

Parainfluenza virus (PIV) antigens including PIV type 1, 2, and 3, preferably containing hemagglutinin, neuraminidase and/or fusion glycoproteins;

Poliovirus antigens including antigens from a family of picornaviridae, preferably poliovirus antigens such as OPV or, preferably IPV;

Measles antigens including split measles virus (MV) antigen optionally combined with the Protollin and or antigens present in MMR vaccine;

Mumps antigens including antigens present in MMR vaccine;

Rubella antigens including antigens present in MMR vaccine as well as other antigens from Togaviridae, including dengue virus;

Rabies such as lyophilized inactivated virus (RabAvert™);

Flaviviridae viruses such as (and antigens derived therefrom) yellow fever virus, Japanese encephalitis virus, dengue virus (types 1, 2, 3, or 4), tick borne encephalitis virus, and West Nile virus;

Caliciviridae antigens therefrom;

Rotavirus including VP4, VP5, VP6, VP7, VP8 proteins (Protein Expr Purif. December 2004;38(2):205) and/or NSP4;

Pestivirus antigens such as antigens from classical porcine fever virus, bovine viral diarrhoea virus, and/or border disease virus;

Parvovirus such as parvovirus B19;

Coronavirus antigens including SARS virus antigens, particularly spike protein or proteases therefrom, as well as antigens included in WO 04/92360.

Viral epitopes/antigens include live, attenuated, split, and/or purified versions of any of the aforementioned.

Further sequences may also be derived from non-viral sources, for instance, for instance, sequences encoding bacterial epitopes/antigens, including but not limited to,

*N. meningitides*: a protein antigen from *N. meningitides* serogroup A, C, W135, Y, and/or B (1-7); an outer-membrane vesicle (OMV) preparation from *N. meningitides* serogroup B. (8, 9, 10, 11); a saccharide antigen, including LPS, from *N. meningitides* serogroup A, B, C W135 and/or Y, such as the oligosaccharide from serogroup C (see PCT/US99/09346; PCT IB98/01665; and PCT IB99/00103);

*Streptococcus pneumoniae*: a saccharide or protein antigen, particularly a saccharide from *Streptooccus pneumoniae*;

*Streptococcus agalactiae*: particularly, Group B *streptococcus* antigens;

*Streptococcus pyogenes*: particularly, Group A *streptococcus* antigens;

*Enterococcus faecalis* or *Enterococcus faecium*: Particularly a trisaccharide repeat or other *Enterococcus* derived antigens provided in U.S. Pat. No. 6,756,361;

*Helicobacter pylori*: including: Cag, Vac, Nap, HopX, HopY and/or urease antigen;

*Bordetella pertussis*: such as petussis holotoxin (PT) and filamentous haemagglutinin (FHA) from *B. pertussis*, optionally also combination with pertactin and/or agglutinogens 2 and 3 antigen;

*Staphylococcus aureus*: including *S. aureus* type 5 and 8 capsular polysaccharides optionally conjugated to nontoxic recombinant *Pseudomonas aeruginosa* exotoxin A, such as StaphVAX™, or antigens derived from surface proteins, invasins (leukocidin, kinases, hyaluronidase), surface factors that inhibit phagocytic engulfinent (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin);

*Staphylococcus epidermis*: particularly, *S. epidermidis* slime-associated antigen (SAA);

*Staphylococcus saprophyticus*: (causing urinary tract infections) particularly the 160 kDa hemagglutinin of *S. saprophyticus* antigen;

*Pseudomonas aeruginosa*: particularly, endotoxin A, Wzz protein, *P. aeruginosa* LPS, more particularly LPS isolated from PAO1 (O5 serotype), and/or Outer Membrane Proteins, including Outer Membrane Proteins F (OprF) (*Infect Immun*. May 2001; 69(5): 3510-3515);

*Bacillus anthracis* (anthrax): such as *B. anthracis* antigens (optionally detoxified) from A-components (lethal factor (LF) and edema factor (EF)), both of which can share a common B-component known as protective antigen (PA);

*Moraxella catarrhalis*: (respiratory) including outer membrane protein antigens (HMW-OMP), C-antigen, and/or LPS;

*Yersinia pestis* (plague): such as F1 capsular antigen (*Infect Immun*. January 2003; 71(1)): 374-383, LPS (*Infect Immun*. October 1999; 67(10): 5395), *Yersinia pestis* V antigen (*Infect Immun*. November 1997; 65(11): 4476-4482);

*Yersinia enterocolitica* (gastrointestinal pathogen): particularly LPS (*Infect Immun*. August 2002; 70(8): 4414);

*Yersinia pseudotuberculosis*: gastrointestinal pathogen antigens;

*Mycobacterium tuberculosis*: such as lipoproteins, LPS, BCG antigens, a fusion protein of antigen 85B (Ag85B) and/or ESAT-6 optionally formulated in cationic lipid vesicles (*Infect Immun*. October 2004; 72(10): 6148), *Mycobacterium tuberculosis* (Mtb) isocitrate dehydrogenase associated antigens (*Proc Natl Acad Sci USA*. Aug. 24, 2004; 101(34): 12652), and/or MPT51 antigens (*Infect Immun*. July 2004; 72(7): 3829);

*Legionella pneumophila* (Legionnairs' Disease): *L. pneumophila* antigens—optionally derived from cell lines with disrupted asd genes (*Infect Immun*. May 1998; 66(5): 1898);

Rickettsia: including outer membrane proteins, including the outer membrane protein A and/or B (OmpB) (*Biochim Biophys Acta*. Nov. 1, 2004;1702(2): 145), LPS, and surface protein antigen (SPA) (*J Autoimmun*. June 1989;2 Suppl:81);

*E. coli*: including antigens from enterotoxigenic *E. coli* (ETEC), enteroaggregative *E. coli* (EAggEC), diffusely adhering *E. coli* (DAEC), enteropathogenic *E. coli* (EPEC), and/or enterohemorrhagic *E. coli* (EHEC);

*Vibrio cholerae*: including proteinase antigens, LPS, particularly lipopolysaccharides of *Vibrio cholerae* II, O1 Inaba O-specific polysaccharides, *V. cholera* O139, antigens of IEM108 vaccine (*Infect Immun*. October 2003;71(10):5498-504), and/or Zonula occludens toxin (Zot);

*Salmonella typhi* (typhoid fever): including capsular polysaccharides preferably conjugates (Vi, i.e. vax-TyVi);

*Salmonella typhimurium* (gastroenteritis): antigens derived therefrom are contemplated for microbial and cancer therapies, including angiogenesis inhibition and modulation of flk;

*Listeria monocytogenes* (systemic infections in immunocompromised or elderly people, infections of fetus): antigens derived from *L. monocytogenes* are preferably used as carriers/vectors for intracytoplasmic delivery of conjugates/associated compositions of the present invention;

*Porphyromonas gingivalis*: particularly, *P. gingivalis* outer membrane protein (OMP);

Tetanus: such as tetanus toxoid (TT) antigens, preferably used as a carrier protein in conjunction/conjugated with the compositions of the present invention;

Diphtheria: such as a diphtheria toxoid, preferably $CRM_{197}$, additionally antigens capable of modulating, inhibiting or associated with ADP ribosylation are contemplated for combination/co-administration/conjugation with the compositions of the present invention, the diphtheria toxoids are preferably used as carrier proteins;

*Borrelia burgdorferi* (Lyme disease): such as antigens associated with P39 and P13 (an integral membrane protein, *Infect Immun*. May 2001; 69(5): 3323-3334), VlsE Antigenic Variation Protein (*J Clin Microbiol*. December 1999; 37(12): 3997);

*Haemophilus influenzae* B: such as a saccharide antigen therefrom;

*Klebsiella*: such as an OMP, including OMP A, or a polysaccharide optionally conjugated to tetanus toxoid;

*Neiserria gonorrhoeae*: including, a Por (or porin) protein, such as PorB (see Zhu et al., Vaccine (2004) 22:660-669), a transferring binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al., J Infectious Disease (2000) 182:848-855), also see e.g. WO99/24578, WO99/36544, WO99/57280, WO02/079243);

*Chlamydia pneumoniae*: particularly *C. pneumoniae* protein antigens;

*Chlamydia trachomatis*: including antigens derived from serotypes A, B, Ba and C are (agents of trachoma, a cause of blindness), serotypes $L_1$, $L_2$ & $L_3$ (associated with *Lymphogranuloma venereum*), and serotypes, D-K;

*Treponema pallidum* (Syphilis): particularly a TmpA antigen; and

*Haemophilus ducreyi* (causing chancroid): including outer membrane protein (DsrA).

Where not specifically referenced, further bacterial antigens may be capsular antigens, polysaccharide antigens or protein antigens of any of the above. Further bacterial antigens may also include an outer membrane vesicle (OMV) preparation. Additionally, antigens include live, attenuated, split, and/or purified versions of any of the aforementioned bacteria. The bacterial or microbial derived antigens may be gram-negative or gram-positive and aerobic or anaerobic. Additionally, any of the above bacterial-derived saccharides (polysaccharides, LPS, LOS or oligosaccharides) can be conjugated to another agent or antigen, such as a carrier protein (for example $CRM_{197}$). Such conjugation may be direct conjugation effected by reductive amination of carbonyl moieties on the saccharide to amino groups on the protein, as provided in US Pat. No. 5,360,897 and *Can J Biochem Cell Biol*. May 1984;62(5):270-5. Alternatively, the saccharides can be conjugated through a linker, such as, with succinamide or other linkages provided in *Bioconjugate Techniques*, 1996 and *CRC, Chemistry of Protein Conjugation and Cross-Linking*, 1993.

Further sequences may also be those encoding fungal antigens, including those described in: U.S. Pat. Nos. 4,229,434 and 4,368,191 for prophylaxis and treatment of trichopytosis caused by *Trichophyton mentagrophytes*; U.S. Pat. Nos. 5,277,904 and 5,284,652 for a broad spectrum dermatophyte vaccine for the prophylaxis of dermatophyte infection in animals, such as guinea pigs, cats, rabbits, horses and lambs, these antigens comprises a suspension of killed *T. equinum, T. mentagrophytes* (var. *granulare*), *M. canis* and/or *M. gypseum* in an effective amount optionally combined with an adjuvant; U.S. Pat. Nos. 5,453,273 and 6,132,733 for a ringworm vaccine comprising an effective amount of a homogenized, formaldehyde-killed fungi, i.e., *Microsporum canis* culture in a carrier; U.S. Pat. No. 5,948,413 involving extracellular and intracellular proteins for pythiosis. Additional antigens identified within antifungal vaccines include Ringvac bovis LTF-130 and Bioveta.

Further, fungal antigens for use herein may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*.

Fungal pathogens for use as antigens or in derivation of antigens in conjunction with the compositions of the present invention comprise *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiospermum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, and *Saksenaea* spp.

Other fungi from which antigens are derived include *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Processes for producing a fungal antigens are well known in the art (see U.S. Pat. No. 6,333,164). In a preferred method a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

Further sequences (e.g., transgenes) also include, but are not limited to, sequences encoding tumor antigens/epitopes. Tumor antigens can be, for example, peptide-containing tumor antigens, such as a polypeptide tumor antigen or glycoprotein tumor antigens. A tumor antigen can also be, for example, a saccharide-containing tumor antigen, such as a glycolipid tumor antigen or a ganglioside tumor antigen. The tumor antigen can further be, for example, a polynucleotide-containing tumor antigen that expresses a polypeptide-containing tumor antigen, for instance, an RNA vector construct or a DNA vector construct, such as plasmid DNA. Tumor antigens encompass a wide variety of molecules, such as (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including poly-saccharides, mucins, gangliosides, glycolipids and glycoproteins, and (c) polynucleotides that express antigenic polypeptides.

The tumor antigens can be, for example, (a) full length molecules associated with cancer cells, (b) homologs and modified forms of the same, including molecules with deleted, added and/or substituted portions, and (c) fragments of the same. Tumor antigens can be provided in recombinant form. Tumor antigens include, for example, class I-restricted antigens recognized by CD8+ lymphocytes or class II-restricted antigens recognized by CD4+ lymphocytes.

Numerous tumor antigens are known in the art, including: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MCIR, melanocyte-stimulating hormone receptor, tyrosinase, tyrosinase related protein-1/TRP 1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Le$^x$ (associated with, e.g., breast and colorectal cancer) as well as various mucins; glycoproteins may be coupled to a carrier protein (e.g., MUC-1 may be coupled to KLH); (ii) lipopolypeptides (e.g., MUC-1 linked to a lipid moiety); (iii) polysaccharides (e.g., Globo H synthetic hexasaccharide), which may be coupled to a carrier proteins (e.g., to KLH), (iv) gangliosides such as GM2, GM12, GD2, GD3 (associated with, e.g., brain, lung cancer, melanoma), which also may be coupled to carrier proteins (e.g., KLH).

Additional tumor antigens which are known in the art include p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like. These as well as other cellular components are described for example in U.S. patent application 20020007173 and references cited therein.

Polynucleotide-containing antigens in accordance with the present invention typically comprise polynucleotides that encode polypeptide cancer antigens such as those listed above. Preferred polynucleotide-containing antigens include DNA or RNA vector constructs, such as plasmid vectors (e.g., pCMV), which are capable of expressing polypeptide cancer antigens in vivo.

Tumor antigens may be derived, for example, from mutated or altered cellular components. After alteration, the cellular components no longer perform their regulatory functions, and hence the cell may experience uncontrolled growth. Representative examples of altered cellular components include ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor. These as well as other cellular components are described for example in U.S. Pat. No. 5,693,522 and references cited therein.

Additional information on cancer or tumor antigens can be found, for example, in Moingeon P, "Cancer vaccines," Vaccine, 2001, 19:1305-1326; Rosenberg S A, "Progress in human tumor immunology and immunotherapy," Nature, 2001, 411:380-384; Dermine, S. et al, "Cancer Vaccines and Immunotherapy," British Medical Bulletin, 2002, 62, 149-162; Espinoza-Delgado I., "Cancer Vaccines," The Oncologist, 2002, 7(suppl3):20-33; Davis, I. D. et al., "Rational approaches to human cancer immunotherapy," Journal of Leukocyte Biology, 2003, 23: 3-29; Van den Eynde B, et al., "New tumor antigens recognized by T cells," Curr. Opin. Immunol., 1995, 7:674-81; Rosenberg S A, "Cancer vaccines based on the identification of genes encoding cancer regression antigens, Immunol. Today, 1997, 18:175-82; Offringa R et al., "Design and evaluation of antigen-specific vaccination strategies against cancer," Current Opin. Immunol., 2000, 2:576-582; Rosenberg S A, "A new era for cancer immunotherapy based on the genes that encode cancer antigens," Immunity, 1999, 10:281-7; Sahin U et al., "Serological identification of human tumor antigens," Curr. Opin. Immunol., 1997, 9:709-16; Old L J et al., "New paths in human cancer serology," J. Exp. Med., 1998, 187:1163-7; Chaux P, et al., "Identification of MAGE-3 epitopes presented by HLA-DR molecules to CD4(+) T lymphocytes," J. Exp. Med., 1999, 189:767-78; Gold P, et al., "Specific carcinoembryonic antigens of the human digestive system," J. Exp. Med., 1965, 122:467-8; Livingston P O, et al., Carbohydrate vaccines that induce antibodies against cancer: Rationale," Cancer Immunol. Immunother., 1997, 45:1-6; Livingston P O, et al., Carbohydrate vaccines that induce antibodies against cancer: Previous experience and future plans," Cancer Immunol. Immunother., 1997, 45:10-9; Taylor-Papadimitriou J, "Biology, biochemistry and immunology of carcinoma-associated mucins," Immunol. Today, 1997, 18:105-7; Zhao X-J et al., "GD2 oligosaccharide: target for cytotoxic T lymphocytes," J. Exp. Med., 1995, 182:67-74; Theobald M, et al., "Targeting p53 as a general tumor antigen," Proc. Natl. Acad. Sci. USA, 1995, 92:11993-7; Gaudemack G, "T cell responses against mutant ras: a basis for novel cancer vaccines," Immunotechnology, 1996, 2:3-9; WO 91/02062; U.S. Pat. No. 6,015,567; WO 01/08636; WO 96/30514; U.S. Pat. No. 5,846,538; and U.S. Pat. No. 5,869,445.

Further sequences also include sequences encoding cytokines such interleukin-2 (IL-2), stem cell factor (SCF), interleukin 3 (IL-3), interleukin 6 (IL-6), interleukin 12 (IL-12), G-CSF, granulocyte macrophage-colony stimulating factor (GM-CSF), interleukin-1 alpha (IL-1), interleukin-11 (IL-11), MIP-1 , tumor necrosis factor (TNF), leukemia inhibitory factor (LIF), c-kit ligand, thrombopoietin (TPO) and flt3 ligand, commercially available from several vendors such as, for example, Genzyme (Framingham, Mass.), Genentech (South San Francisco, Calif.), Amgen (Thousand Oaks, Calif.), R&D Systems and Immunex (Seattle, Wash.). Additional sequences are described below. Also, variations on the orientation of the Gag and other coding sequences, relative to each other, are described below.

Although exemplified with regard to subtype B isolate SF2, it will be apparent that sequences as described herein can readily be derived from other HIV isolates, see, e.g., Myers et al. Los Alamos Database, Los Alamos National Laboratory, Los Alamos, N. Mex. (1992); Myers et al., *Human Retroviruses and Aids,* 1997, Los Alamos, N. Mex.: Los Alamos National Laboratory. Synthetic expression cassettes can be generated using such coding sequences as starting material by following the teachings of the present specification.

5. Expression of Synthetic Sequences

The synthetic sequences encoding HIV polypeptides described herein increase expression and secretion of HIV polypeptides. In particular, sequences including Gag, pol, tat, rev and nef expressed as a polyprotein are disclosed. Many of these sequences exhibit increased expression and secretion as compared to sequences encoding wild-type. Data shown below also indicates that when expressed as a polyprotein, the sequences may exhibit increased expression of polypeptides as compared to expression obtained from modified (synthetic) Gag- and poll-encoding sequences. Furthermore, constructs as described herein in which sequences encoding Tat, rev and/or nef are 5' relative to sequences encoding Gag and/or Pol may exhibit increased expression and secretion as compared to constructs having the reverse orientation (i.e., Tat, rev and/or nef are 3' relative to sequences encoding Gag and/or Pol).

Preferably, the multiple sequences are cloned in-frame into a single vector such that multiple polynucleotides encoding a more than one gene product (or portion thereof) (e.g., polycistronic coding sequences) to produce a single polyprotein. Optionally, the polyprotein may protein cleavage sites between one or more of the polypeptides comprising the polyprotein.

The present invention also includes co-transfection with multiple, monocistronic expression cassettes, as well as, co-transfection with one or more multi-cistronic expression cassettes, or combinations thereof. For example, a bicistronic construct may be made where the coding sequences for the different HIV polypeptides are under the control of a single CMV promoter and, between the two coding sequences, an IRES (internal ribosome entry site (EMCV IRES); Kozak, M., Critical Reviews in Biochemistry and Molecular Biology 27(45):385-402, 1992; Witherell, G. W., et al., Virology 214: 660-663, 1995) sequence is introduced after the first HIV coding sequence and before the second HIV coding sequence.

To evaluate expression levels and/or secretion, sequences described herein can be cloned into a number of different vectors including but not limited to, prokaryotic vectors and eukaryotic expression vectors, including, a transient expression vector, CMV-promoter-based mammalian vectors, and a shuttle vector for use in baculovirus expression systems.

Insect cell expression systems, such as baculovirus systems, are known to those of skill in the art and described in, e.g., Summers and Smith, *Texas Agricultural Experiment Station Bulletin* No. 1555 (1987). Materials and methods for baculovirus/insect cell expression systems are commercially available in kit form from, inter alia, Invitrogen, San Diego Calif. Similarly, bacterial and mammalian cell expression systems are also known in the art and described in, e.g., *Yeast Genetic Engineering* (Barr et al., eds., 1989) Butterworths, London.

These vectors can then be transfected into a several different cell types, including a variety of mammalian cell lines (293, RD, COS-7, and CHO, cell lines available, for example, from the A.T.C.C.). The cell lines are then cultured under appropriate conditions and the levels of any appropriate polypeptide product can be evaluated in supernatants. For example, p24 or p55 can be used to determine Gag expression. Further, modified polypeptides can also be used, for example, other Gag polypeptides. The results of these assays demonstrate that expression of synthetic HIV polypeptide-encoding sequences are significantly higher than corresponding wild-type sequences.

Further, Western Blot analysis can be used to show that cells comprising the synthetic polynucleotides (e.g., expression cassettes comprising these polynucleotides) produce the expected protein at higher per-cell concentrations than cells containing the native sequences. Protein analysis can be conducted using any suitable assay, for example the Odyssey™ Infrared Antibody Detection Systems (Li-Cor Biosciences, Lincoln, Nebr.). The HIV proteins can be seen in both cell lysates and supernatants. (Example 3, FIGS. 3 and 4).

Fractionation of the supernatants from mammalian cells transfected as described herein can be used to show that vectors comprising the synthetic sequences described herein provide superior production of HIV proteins.

Efficient expression of these HIV-containing polypeptides in mammalian cell lines provides the following benefits: increased secretion may lead to increased uptake of proteins by antigen presenting cells, which in turn may lead to increased immunogenicity, for example when delivered (e.g., subcutaneously, intradermally, or mucosally) to APC-rich environment; increased expression may lead to increased priming efficiency and/or increased cross-priming efficiency (where cells adjacent to those which take up the DNA are also primed), for example in combination with alphavirus replicons; the polypeptides are free of baculovirus contaminants; production by established methods approved by the FDA; increased purity; greater yields (relative to native coding sequences); and a novel method of producing the HIV-containing polypeptides in CHO cells which is not feasible in the absence of the increased expression (as compared, for example, to native sequences) obtained using the constructs of the present invention.

Mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (e.g., Hep G2), Madin-Darby bovine kidney ("MDBK") cells, PERC.6 cells which are described, for example, in WO 01/38362 and WO 02/40665, incorporated by reference herein in their entireties, as well as deposited under ECACC deposit number 96022940), as well as others.

Mammalian sources of cells include, but are not limited to, human or non-human primate (e.g., MRC-5 (ATCC CCL-171), WI-38 (ATCC CCL-75), fetal rhesus lung cells (ATCC CL-160), human embryonic kidney cells (293 cells, typically transformed by sheared adenovirus type 5 DNA), VERO cells from monkey kidneys), horse, cow (e.g., MDBK cells), sheep, dog (e.g., MDCK cells from dog kidneys, ATCC CCL34 MDCK (NBL2) or MDCK 33016, deposit number DSM ACC 2219 as described in WO 97/37001), cat, and rodent (e.g., hamster cells such as BHK21-F, HKCC cells, or Chinese hamster ovary cells (CHO cells)), and may be obtained from a wide variety of developmental stages, including for example, adult, neonatal, fetal, and embryo.

Other exemplary Mammalian cell lines include, but are not limited to, HT1080, RD, COS-7, Jurkat, HUT, SUPT, C8166, MOLT4/clone8, MT-2, MT-4, H9, PM1, CEM, and CEMX174, such cell lines are available, for example, from the A.T.C.C.). Insect cells for use with baculovirus expression vectors include, inter alia, *Aedes aegypti, Autographa californica, Bombyx mori, Drosophila melanogaster, Spodoptera frugiperda*, and *Trichoplusia ni*.

Further, synthetic sequences of the present invention can also be introduced into yeast vectors which, in turn, can be transformed into and efficiently expressed by yeast cells (*Saccharomyces cerevisea*; using vectors as described in Rosenberg, S. and Tekamp-Olson, P., U.S. Pat. No. RE35,749, issued, Mar. 17, 1998, herein incorporated by reference). Yeast cells include, inter alia, *Saccharomyces cerevisiae, Candida albicans, Candida maltosa, Hansenual polymorpha, Kluyveromyces fragilis, Kluyveromyces lactis, Pichia guillerimondii, Pichia pastoris, Schizosaccharomyces pombe* and *Yarrowia lipolytica*.

In addition to the mammalian and insect vectors, the synthetic polynucleotides of the present invention can also be produced (expressed) using an avian expression system. Avian cell expression systems are known in the art and described in, e.g., U.S. Pat. Nos. 5,340,740; 5,656,479; 5,830,510; 6,114,168; and 6,500,668; European Patent No. EP 0787180B; WO 03/043415; and WO 03/076601. Avian cell lines are known in the art and include embryonic germ cell lines and embryonic stem (ES) cell lines. Avian sources of cells include, but are not limited to, chicken ES cells (EBx® cell lines), chicken EG cells, turkey ES or EG cells, quail ES or EG cells, pheasant ES or EG cells.

In addition to the mammalian, avian and insect vectors, the synthetic polynucleotides of the present invention can be incorporated into a variety of expression vectors using selected expression control elements. Appropriate vectors and control elements for any given cell type can be selected by one having ordinary skill in the art in view of the teachings of the present specification and information known in the art.

For example, a suitable vector may include control elements operably linked to the desired coding sequence, which allow for the expression of the gene in a selected cell-type. For example, typical promoters for mammalian cell expression include the SV40 early promoter, a CMV promoter such as the CMV immediate early promoter (a CMV promoter can include intron A), RSV, HIV-Ltr, the mouse mammary tumor virus LTR promoter (MMLV-ltr), the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook, et al., supra, as well as a bovine growth hormone terminator sequence. Introns, containing splice donor and acceptor sites, may also be designed into the constructs for use with the present invention (Chapman et al., Nuc. Acids Res. (1991) 19:3979-3986).

Enhancer elements may also be used herein to increase expression levels of the mammalian constructs. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence (Chapman et al., Nuc. Acids Res. (1991) 19:3979-3986).

The desired synthetic polypeptide encoding sequences can be cloned into any number of commercially available vectors to generate expression of the polypeptide in an appropriate host system. These systems include, but are not limited to, the following: baculovirus expression {Reilly, P. R., et al., Baculovirus Expression Vectors: A Laboratory Manual (1992); Beames, et al., Biotechniques 11:378 (1991); Pharmingen; Clontech, Palo Alto, Calif.)}, vaccinia expression {Earl, P. L., et al., "Expression of proteins in mammalian cells using vaccinia" In Current Protocols in Molecular Biology (F. M. Ausubel, et al. Eds.), Greene Publishing Associates & Wiley Interscience, New York (1991); Moss, B., et al., U.S. Pat. No. 5,135,855, issued 4 Aug. 1992}, expression in bacteria {Ausubel, F. M., et al., Current Protocols in Molecular Biology, John Wiley and Sons, Inc., Media Pa.; Clontech}, expression in yeast {Rosenberg, S. and Tekamp-Olson, P., U.S. Pat. No. RE35,749, issued, Mar. 17, 1998, herein incorporated by reference; Shuster, J. R., U.S. Pat. No. 5,629,203, issued May 13, 1997, herein incorporated by reference; Gellissen, G., et al., Antonie Van Leeuwenhoek, 62(1-2):79-93 (1992); Romanos, M. A., et al., Yeast 8(6):423-488 (1992); Goeddel, D. V., Methods in Enzymology 185 (1990); Guthrie, C., and G. R. Fink, Methods in Enzymology 194 (1991)}, expression in mammalian cells {Clontech; Gibco-BRL, Ground Island, N.Y.; e.g., Chinese hamster ovary (CHO) cell lines (Haynes, J., et al., Nuc. Acid. Res. 11:687-706 (1983); 1983, Lau, Y. F., et al., Mol. Cell. Biol. 4:1469-1475 (1984); Kaufman, R. J., "Selection and coamplification of heterologous genes in mammalian cells," in Methods in Enzymology, vol. 185, pp 537-566. Academic Press, Inc., San Diego Calif. (1991)}, and expression in plant cells {plant cloning vectors, Clontech Laboratories, Inc., Palo Alto, Calif., and Pharmacia LKB Biotechnology, Inc., Pistcataway, N.J.; Hood, E., et al., J. Bacteriol. 168:1291-1301 (1986); Nagel, R., et al., FEMS Microbiol. Lett. 67:325 (1990); An, et al., "Binary Vectors", and others in Plant Molecular Biology Manual A3:1-19 (1988); Miki, B. L. A., et al., pp. 249-265, and others in Plant DNA Infectious Agents (Hohn, T., et al., eds.) Springer-Verlag, Wien, Austria, (1987); Plant Molecular Biology: Essential Techniques, P. G. Jones and J. M. Sutton, New York, J. Wiley, 1997; Miglani, Gurbachan Dictionary of Plant Genetics and Molecular Biology, New York, Food Products Press, 1998; Henry, R. J., Practical Applications of Plant Molecular Biology, New York, Chapman & Hall, 1997}.

As noted above, the expression vectors typically contain coding sequences and expression control elements that allow expression of the coding regions in a suitable host. The control elements generally include a promoter, translation initiation codon, and translation and transcription termination sequences, and an insertion site for introducing the insert into the vector. Translational control elements have been reviewed by M. Kozak (e.g., Kozak, M., Mamm. Genome 7(8):563-574, 1996; Kozak, M., Biochimie 76(9):815-821, 1994; Kozak, M., J Cell Biol 108(2):229-241, 1989; Kozak, M., and Shatkin, A. J., Methods Enzymol 60:360-375, 1979).

Expression in yeast systems has the advantage of commercial production. Recombinant protein production by vaccinia and CHO cell line has the advantage of being mammalian expression systems. Further, vaccinia virus expression has several advantages including the following: (i) its wide host range; (ii) faithful post-transcriptional modification, processing, folding, transport, secretion, and assembly of recombinant proteins; (iii) high level expression of relatively soluble recombinant proteins; and (iv) a large capacity to accommodate foreign DNA.

The recombinantly expressed polypeptides from synthetic HIV polypeptide-encoding sequences are typically isolated from lysed cells or culture media. Purification can be carried out by methods known in the art including salt fractionation, ion exchange chromatography, gel filtration, size-exclusion chromatography, size-fractionation, and affinity chromatography. Immunoaffinity chromatography can be employed using antibodies generated based on, for example, HIV antigens.

Advantages of expressing the proteins of the present invention using mammalian cells include, but are not limited to, the following: well-established protocols for scale-up production; the ability to produce neutralizing antibodies; cell lines are suitable to meet good manufacturing process (GMP) standards; culture conditions for mammalian cells are known in the art.

Synthetic HIV 1 polynucleotides are described herein, see, for example, the figures. Various forms of the different embodiments of the invention, described herein, may be combined.

6. DNA Immunization and Gene Delivery

DNA immunization using synthetic sequences of the present invention can be performed, for example, as follows. Mice are immunized with an expression cassette comprising, proceeding in a 5' to 3' direction, synthetic tat-, rev- and/or nef-encoding sequences followed by synthetic Gag- and/or Pol-encoding sequences. Other mice are immunized with a tat/rev/nef/Gag/Pol wild type expression cassettes and/or cassettes in which synthetic Gag- and/or Pol-encoding sequences are 5' to synthetic tat-, rev- and/or nef-encoding sequences. Further, animals are preferably immunized with expression cassettes comprising wild type sequences as well as other synthetic sequences (e.g., Gag, Pol, GagPol, TatRev-Nef, etc.).

Other HIV antigens of particular interest to be used in the practice of the present invention include, but are not limited to, Env, vif, vpu, vpr, and other HIV antigens or epitopes derived therefrom. These antigens may be synthetic (as described herein) or wild-type. Further, the packaging cell line may contain only nef, and HIV-1 (also known as HTLV-III, LAV, ARV, etc.), including, but not limited to, antigens (both native and modified) from a variety of isolates including, but not limited to, HIVIIIb, HIVSF2, HIV-1SF162, HIV-1SF170, HIVLAV, HIVLAI, HIVMN, HIV-1CM235, HIV-1US4, other HIV-1 strains from diverse subtypes(e.g., subtypes, A through K, N and O), HIV-2 strains and diverse subtypes (e.g., HIV-2UC1 and HIV-2UC2). See, e.g., Myers, et al., Los Alamos Database, Los Alamos National Laboratory, Los Alamos, N. Mex.; Myers, et al., Human Retroviruses and Aids, 1990, Los Alamos, N. Mex.: Los Alamos National Laboratory.

To evaluate efficacy, DNA immunization can be performed, for instance as described in Example 4. Animals (e.g., mice, guinea pigs, rabbits or non-human primates) are immunized with the polycistronic synthetic sequences (e.g., expression cassettes) having sequences in various 5' to 3' orders, unicistronic synthetic sequences (e.g., Gag or Pol), bicistronic sequences (e.g., GagPol) and the wild type Env sequences. Immunizations with the polynucleotides will show that the synthetic sequences provide a clear improvement of immunogenicity relative to the native sequences. Also, the second boost immunization will induce a secondary immune response, for example, after approximately two weeks.

6.1 Delivery

Polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from cells and tissues containing the same, using standard techniques, such as phenol extraction and PCR of cDNA or genomic DNA. See, e.g., Sambrook et al., supra, for a description of techniques used to obtain and isolate DNA. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence is assembled from overlapping oligonucleotides prepared by standard methods and assembled into a complete coding sequence. See, e.g., Edge, Nature (1981) 292:756; Nambair et al., Science (1984) 223: 1299; Jay et al., J. Biol. Chem. (1984) 259:6311; Stemmer, W. P. C., (1995) Gene 164:49-53.

Next, the gene sequence encoding the desired antigen can be inserted into a vector. The vector can also include control elements operably linked to the coding sequence, which allow for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence.

Enhancer elements may also be used herein to increase expression levels of the mammalian constructs. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

Furthermore, plasmids can be constructed which include a chimeric antigen-coding gene sequences, encoding, e.g., multiple antigens/epitopes of interest, for example derived from more than one viral isolate.

The antigen coding sequences precede or follow the synthetic coding sequence and the chimeric transcription unit an may have a single open reading frame encoding both the antigen of interest and the synthetic coding sequences. Alternatively, polycistronic cassettes can be constructed allowing expression of multiple antigens from a single mRNA using the EMCV IRES, or the like.

Once complete, the constructs are used for nucleic acid immunization using standard gene delivery protocols. Methods for gene delivery are known in the art. See, e.g., U.S. Pat. Nos. 5,399,346, 5,580,859, 5,589,466. Genes can be delivered either directly to the vertebrate subject or, alternatively, delivered ex vivo, to cells derived from the subject and the cells reimplanted in the subject.

A number of viral based systems have been developed for gene transfer into mammalian cells. For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219, 740; Miller and Rosman, BioTechniques (1989) 7:980-990; Miller, A. D., Human Gene Therapy (1990) 1:5-14; Scarpa et al., Virology (1991) 180:849-852; Burns et al., Proc. Natl. Acad. Sci. USA (1993) 90:8033-8037; and Boris-Lawrie and Temin, Cur. Opin. Genet. Develop. (1993) 3:102-109.

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476).

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell. Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors that will find use for delivering the nucleic acid molecules encoding the antigens of interest include those derived from the pox family of viruses, including vaccinia virus and avian poxvirus. By way of example, vaccinia virus recombinants expressing the genes can be constructed as follows. The DNA encoding the particular synthetic HIV polypeptide coding sequence is first inserted into an appropriate vector so that it is adjacent to a vaccinia promoter and flanking vaccinia DNA sequences, such as the sequence encoding thymidine kinase (TK). This vector is then used to transfect cells that are simultaneously infected with vaccinia. Homologous recombination serves to insert the vaccinia promoter plus the gene encoding the coding sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the Alphavirus genus, such as, but not limited to, vectors derived from the Sindbis, Semliki Forest, and Venezuelan Equine Encephalitis viruses, will also find use as viral vectors for delivering the polynucleotides of the present invention (for example, a synthetic Env-polypeptide encoding expression cassette). For a description of Sindbis-virus derived vectors useful for the practice of the instant methods, see, Dubensky et al., J. Virol. (1996) 70:508-519; and International Publication Nos. WO 95/07995 and WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference.

A vaccinia based infection/transfection system can be conveniently used to provide for inducible, transient expression of the coding sequences of interest in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA that is then translated into protein by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase that in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, J. Mol. Biol. (1986) 189:113-130; Deng and Wolff, Gene (1994) 143:245-249; Gao et al., Biochem. Biophys. Res. Commun. (1994) 200: 1201-1206; Gao and Huang, Nuc. Acids Res. (1993) 21:2867-2872; Chen et al., Nuc. Acids Res. (1994) 22:2114-2120; and U.S. Pat. No. 5,135,855.

Synthetic sequences of interest can also be delivered without a viral vector. For example, the synthetic sequences (or expression cassettes) can be packaged in liposomes prior to delivery to the subject or to cells derived therefrom. Lipid encapsulation is generally accomplished using liposomes that are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, Biochim. Biophys. Acta. (1991) 1097:1-17; Straubinger et al., in Methods of Enzymology (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Felgner et al., Proc. Natl. Acad. Sci. USA (1987) 84:7413-7416); mRNA (Malone et al., Proc. Natl. Acad. Sci. USA (1989) 86:6077-6081); and purified transcription factors (Debs et al., J. Biol. Chem. (1990) 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., Proc. Natl. Acad. Sci. USA (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., Proc. Natl. Acad. Sci. USA (1978) 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., Proc. Natl. Acad. Sci. USA (1978) 75:4194-4198; Papahadjopoulos et al., Biochim. Biophys. Acta (1975) 394:483; Wilson et al., Cell (1979) 17:77); Deamer and Bangham, Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); Enoch and Strittmatter, Proc. Natl. Acad. Sci. USA (1979) 76:145); Fraley et al., J. Biol. Chem. (1980) 255:10431; Szoka and Papahadjopoulos, Proc. Natl. Acad. Sci. USA (1978) 75:145; and Schaefer-Ridder et al., Science (1982) 215:166.

The DNA and/or protein antigen(s) can also be delivered in cochleate lipid compositions similar to those described by Papahadjopoulos et al., Biochem. Biophys. Acta. (1975) 394:483-491. See, also, U.S. Pat. Nos. 4,663,161 and 4,871,488.

The synthetic sequences (and/or expression cassettes) of interest may also be encapsulated, adsorbed to, or associated with, particulate carriers. Such carriers present multiple copies of a selected antigen to the immune system and promote trapping and retention of antigens in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; McGee J P, et al., J Microencapsul. 14(2):197-210, 1997; O'Hagan D T, et al., Vaccine 11(2):149-54, 1993. Suitable microparticles may also be manufactured in the presence of charged detergents, such as anionic or cationic detergents, to yield microparticles with a surface having a net negative or a net positive charge. For example, microparticles manufactured with anionic detergents, such as hexadecyltrimethylammonium bromide (CTAB), i.e. CTAB-PLG microparticles, adsorb negatively charged macromolecules, such as DNA. (see, e.g., Int'l Application Number PCT/US99/17308).

Furthermore, other particulate systems and polymers can be used for the in vivo or ex vivo delivery of the gene of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Felgner, P. L., Advanced Drug Delivery Reviews (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten, are especially useful for delivering synthetic sequences and vectors of the present invention. The particles are coated with the synthetic sequences (and/or expression cassette(s)) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744. Also, needle-less injection systems can be used (Davis, H. L., et al, Vaccine 12:1503-1509, 1994; Bioject, Inc., Portland, Oreg.). Direct delivery of compositions comprising the synthetic sequences described herein in vivo will generally be accomplished with or without viral vectors, as described above, by injection using either a conventional syringe or a gene gun, such as the Accell® gene delivery system (PowderJect Technologies, Inc., Oxford, England).

The constructs can be injected either subcutaneously, epidermally, intradermally, intramucosally such as nasally, rectally and vaginally, intraperitoneally, intravenously, orally or intramuscularly. Delivery of DNA into cells of the epidermis is particularly preferred as this mode of administration provides access to skin-associated lymphoid cells and provides for a transient presence of DNA in the recipient. Other modes of administration include oral and pulmonary administration, suppositories, needle-less injection, transcutaneous and transdermal applications.

The sequences described herein may also be administered using in vivo electroporation techniques. Efficient in vivo expression of plasmid encoded genes by electrical permeabilization (electroporation) has been described (see, e.g., Zucchelli et al. (2000) *J. Virol.* 74:11598-11607; Banga et al. (1998) *Trends Biotechnol.* 10:408-412; Heller et al. (1996) *Febs Lett.* 389:225-228; Mathiesen et al. (1999) *Gene Ther.* 4:508-514; Mir et al. (1999) *Proc. Nat'l Acad Sci. USA* 8:4262-4267; Nishi et al. (1996) *Cancer Res.* 5:1050-1055).

6.2 Ex vivo Delivery

In one embodiment, T cells, and related cell types (including but not limited to antigen presenting cells, such as, macrophage, monocytes, lymphoid cells, dendritic cells, B-cells, T-cells, stem cells, and progenitor cells thereof), can be used for ex vivo delivery of the synthetic sequences of the present invention. T cells can be isolated from peripheral blood lymphocytes (PBLs) by a variety of procedures known to those skilled in the art. For example, T cell populations can be "enriched" from a population of PBLs through the removal of accessory and B cells. In particular, T cell enrichment can be accomplished by the elimination of non-T cells using anti-MHC class II monoclonal antibodies. Similarly, other antibodies can be used to deplete specific populations of non-T cells. For example, anti-Ig antibody molecules can be used to deplete B cells and anti-MacI antibody molecules can be used to deplete macrophages.

T cells can be further fractionated into a number of different subpopulations by techniques known to those skilled in the art. Two major subpopulations can be isolated based on their differential expression of the cell surface markers CD4 and CD8. For example, following the enrichment of T cells as described above, CD4+ cells can be enriched using antibodies specific for CD4 (see Coligan et al., supra). The antibodies may be coupled to a solid support such as magnetic beads. Conversely, CD8+ cells can be enriched through the use of antibodies specific for CD4 (to remove CD4+ cells), or can be isolated by the use of CD8 antibodies coupled to a solid support. CD4 lymphocytes from HIV-1 infected patients can be expanded ex vivo, before or after transduction as described by Wilson et. al. (1995) J. Infect. Dis. 172:88.

Following purification of T cells, a variety of methods of genetic modification known to those skilled in the art can be performed using non-viral or viral-based gene transfer vectors constructed as described herein. For example, one such approach involves transduction of the purified T cell population with vector-containing supernatant of cultures derived from vector producing cells. A second approach involves co-cultivation of an irradiated monolayer of vector-producing cells with the purified T cells. A third approach involves a similar co-cultivation approach; however, the purified T cells are pre-stimulated with various cytokines and cultured 48 hours prior to the co-cultivation with the irradiated vector producing cells. Pre-stimulation prior to such transduction increases effective gene transfer (Nolta et al. (1992) Exp. Hematol. 20:1065). Stimulation of these cultures to proliferate also provides increased cell populations for re-infusion into the patient. Subsequent to co-cultivation, T cells are collected from the vector producing cell monolayer, expanded, and frozen in liquid nitrogen.

Gene transfer vectors, containing one or more synthetic sequences of the present invention (associated with appropriate control elements for delivery to the isolated T cells) can be assembled using known methods.

Selectable markers can also be used in the construction of gene transfer vectors. For example, a marker can be used which imparts to a mammalian cell transduced with the gene transfer vector resistance to a cytotoxic agent. The cytotoxic agent can be, but is not limited to, neomycin, aminoglycoside, tetracycline, chloramphenicol, sulfonamide, actinomycin, netropsin, distamycin A, anthracycline, or pyrazinamide. For example, neomycin phosphotransferase II imparts resistance to the neomycin analogue geneticin (G418).

The T cells can also be maintained in a medium containing at least one type of growth factor prior to being selected. A variety of growth factors are known in the art that sustain the growth of a particular cell type. Examples of such growth factors are cytokine mitogens such as rIL-2, IL-10, IL-1 2, and IL-1 5, which promote growth and activation of lymphocytes. Certain types of cells are stimulated by other growth factors such as hormones, including human chorionic gonadotropin (hCG) and human growth hormone. The selection of an appropriate growth factor for a particular cell population is readily accomplished by one of skill in the art.

For example, white blood cells such as differentiated progenitor and stem cells are stimulated by a variety of growth factors. More particularly, IL-3, IL-4, IL-5, IL-6, IL-9, GM-CSF, M-CSF, and G-CSF, produced by activated TH and activated macrophages, stimulate myeloid stem cells, which then differentiate into pluripotent stem cells, granulocyte-monocyte progenitors, eosinophil progenitors, basophil progenitors, megakaryocytes, and erythroid progenitors. Differentiation is modulated by growth factors such as GM-CSF, IL-3, IL-6, IL-11, and EPO.

Pluripotent stem cells then differentiate into lymphoid stem cells, bone marrow stromal cells, T cell progenitors, B cell progenitors, thymocytes, TH Cells, TC cells, and B cells. This differentiation is modulated by growth factors such as IL-3, IL-4, IL-6, IL-7, GM-CSF, M-CSF, G-CSF, IL-2, and IL-5.

Granulocyte-monocyte progenitors differentiate to monocytes, macrophages, and neutrophils. Such differentiation is modulated by the growth factors GM-CSF, M-CSF, and IL-8. Eosinophil progenitors differentiate into eosinophils. This process is modulated by GM-CSF and IL-5.

The differentiation of basophil progenitors into mast cells and basophils is modulated by GM-CSF, IL-4, and IL-9. Megakaryocytes produce platelets in response to GM-CSF, EPO, and IL-6. Erythroid progenitor cells differentiate into red blood cells in response to EPO.

Thus, during activation by the CD3-binding agent, T cells can also be contacted with a mitogen, for example a cytokine such as IL-2. In particularly preferred embodiments, the IL-2 is added to the population of T cells at a concentration of about 50 to 100 µg/ml. Activation with the CD3-binding agent can be carried out for 2 to 4 days.

Once suitably activated, the T cells are genetically modified by contacting the same with a suitable gene transfer vector under conditions that allow for transfection of the vectors into the T cells. Genetic modification is carried out when the cell density of the T cell population is between about $0.1 \times 10^6$ and $5 \times 10^6$, preferably between about $0.5 \times 10^6$ and $2 \times 10^6$. A number of suitable viral and nonviral-based gene transfer vectors have been described for use herein.

After transduction, transduced cells are selected away from non-transduced cells using known techniques. For example, if the gene transfer vector used in the transduction includes a selectable marker that confers resistance to a cytotoxic agent, the cells can be contacted with the appropriate cytotoxic agent, whereby non-transduced cells can be negatively selected away from the transduced cells. If the selectable marker is a cell surface marker, the cells can be contacted with a binding agent specific for the particular cell surface marker, whereby the transduced cells can be positively selected away from the population. The selection step can also entail fluorescence-activated cell sorting (FACS) techniques, such as where FACS is used to select cells from the population containing a particular surface marker, or the selection step can entail the use of magnetically responsive particles as retrievable supports for target cell capture and/or background removal.

More particularly, positive selection of the transduced cells can be performed using a FACS cell sorter (e.g. a FACSVantage™ Cell Sorter, Becton Dickinson Immunocytometry Systems, San Jose, Calif.) to sort and collect transduced cells expressing a selectable cell surface marker. Following transduction, the cells are stained with fluorescent-labeled antibody molecules directed against the particular cell surface marker. The amount of bound antibody on each cell can be measured by passing droplets containing the cells through the cell sorter. By imparting an electromagnetic charge to droplets containing the stained cells, the transduced cells can be separated from other cells. The positively selected cells are then harvested in sterile collection vessels. These cell sorting procedures are described in detail, for example, in the FACSVantage™ Training Manual, with particular reference to sections 3-11 to 3-28 and 10-1 to 10-17.

Positive selection of the transduced cells can also be performed using magnetic separation of cells based on expression or a particular cell surface marker. In such separation techniques, cells to be positively selected are first contacted with specific binding agent (e.g., an antibody or reagent that interacts specifically with the cell surface marker). The cells are then contacted with retrievable particles (e.g., magnetically responsive particles) that are coupled with a reagent that binds the specific binding agent (that has bound to the positive cells). The cell-binding agent-particle complex can then be physically separated from non-labeled cells, for example using a magnetic field. When using magnetically responsive particles, the labeled cells can be retained in a container using a magnetic filed while the negative cells are removed. These and similar separation procedures are known to those of ordinary skill in the art.

Expression of the vector in the selected transduced cells can be assessed by a number of assays known to those skilled in the art. For example, Western blot or Northern analysis can be employed depending on the nature of the inserted nucleotide sequence of interest. Once expression has been established and the transformed T cells have been tested for the presence of the selected synthetic sequence, they are ready for infusion into a patient via the peripheral blood stream.

The invention includes a kit for genetic modification of an ex vivo population of primary mammalian cells. The kit typically contains a gene transfer vector coding for at least one selectable marker and at least one synthetic sequence (e.g., expression cassette) contained in one or more containers, ancillary reagents or hardware, and instructions for use of the kit.

6.3 Further Delivery Regimes

Any of the polynucleotides (e.g., expression cassettes) or polypeptides described herein (delivered by any of the methods described above) can also be used in combination with other DNA delivery systems and/or protein delivery systems. Non-limiting examples include co-administration of these molecules, for example, in prime-boost methods where one or more molecules are delivered in a "priming" step and, subsequently, one or more molecules are delivered in a "boosting" step.

In certain embodiments, the delivery of one or more nucleic acid-containing compositions is followed by delivery of one or more nucleic acid-containing compositions and/or one or more polypeptide-containing compositions (e.g., polypeptides comprising HIV antigens). In other embodiments, the delivery of one or more nucleic acid-containing compositions is preceded by delivery of one or more polypeptide-containing compositions (e.g., polypeptides comprising HIV antigens) and/or one or more nucleic acid-containing compositions. In still other embodiments, multiple nucleic acid "primes" (of the same or different nucleic acid molecules) can be followed by multiple polypeptide "boosts" (of the same or different polypeptides) and/or multiple polynucleotide "boosts" (of the same or different polynucleotides). Other examples include multiple nucleic acid administrations and multiple polypeptide administrations.

In any method involving co-administration, the various compositions can be delivered in any order. Thus, in embodiments including delivery of multiple different compositions or molecules, the nucleic acids need not be all delivered before the polypeptides. For example, the priming step may include delivery of one or more polypeptides and the boosting comprises delivery of one or more nucleic acids and/or one more polypeptides. Multiple polypeptide administrations can be followed by multiple nucleic acid administrations or polypeptide and nucleic acid administrations can be performed in any order. In any of the embodiments described herein, the nucleic acid molecules can encode all, some or none of the polypeptides. Thus, one or more or the nucleic acid molecules (e.g., expression cassettes) described herein and/or one or more of the polypeptides described herein can be co-administered in any order and via any administration routes. Therefore, any combination of polynucleotides and/or polypeptides described herein can be used to generate elicit an immune reaction.

7 Compositions

Recombinant vectors carrying a synthetic sequences of the present invention are typically formulated into compositions for delivery to the vertebrate subject. These compositions may either be prophylactic (to prevent infection) or therapeutic (to treat disease after infection) and may include one or more of the following molecules: polynucleotides, polypeptides, other small molecules and/or other macromolecules. The compositions will comprise a "therapeutically effective amount" of the gene of interest such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials.

The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, and the like, may be present in such vehicles. Certain facilitators of nucleic acid uptake and/or expression can also be included in the compositions or coadministered, such as, but not limited to, bupivacaine, cardiotoxin and sucrose.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; McGee J P, et al., J Microencapsul. 14(2):197-210, 1997; O'Hagan D T, et al., Vaccine 11(2):149-54, 1993. Such carriers are well known to those of ordinary skill in the art. Additionally, these carriers may function as immunostimulating agents ("adjuvants"). Furthermore, the antigen may be conjugated to a bacterial toxoid, such as toxoid from diphtheria, tetanus, cholera, etc., as well as toxins derived from E. coli.

Compositions of the invention may be administered in conjunction with other immunoregulatory agents. In particular, the compositions will usually include an adjuvant. Adjuvants for use with the invention include, but are not limited to, one or more of the following set forth below.

Adjuvants may also be used to enhance the effectiveness of the compositions. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) oligonucleotides or polymeric molecules encoding immunostimulatory CpG motifs (a sequence containing an unmethylated cytosine followed by guanosine and linked by a phosphate bond) (Davis, H. L., et al., J. Immunology 160:870-876, 1998; Sato, Y. et al., Science 273:352-354, 1996) or complexes of antigens/oligonucleotides {Polymeric molecules include double and single stranded RNA and DNA, and backbone modifications thereof, for example, methylphosphonate linkages; or (7) detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. W093/13202 and W092/19265); and (8) other substances that act as immunostimulating agents to enhance the effectiveness of the composition. Further, such polymeric molecules include alternative polymer backbone structures such as, but not limited to, polyvinyl backbones (Pitha, Biochem Biophys Acta, 204:39, 1970a; Pitha, Biopolymers, 9:965, 1970b), and morpholino backbones (Summerton, J., et al., U.S. Pat. No. 5,142,047, issued Aug. 25, 1992; Summerton, J., et al., U.S. Pat. No. 5,185,444 issued Feb. 9, 1993). A variety of other charged and uncharged polynucleotide analogs have been reported. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates).

Other adjuvants include, but are not limited to:

(1) Virosomes and Virus Like Particles (VLPs): These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO03/024480, WO03/024481, and Niikura et al., Virology (2002) 293:273-280; Lenz et al., Journal of Immunology (2001) 5246-5355; Pinto, et al., Journal of Infectious Diseases (2003) 188:327-338; and Gerber et al., Journal of Virology (2001) 75(10):4752-4760. Virosomes are discussed further in, for example, Gluck et al., "New Technology Platforms in the Development of Vaccines for the Future", Vaccine (2002) 20:B10-B16. Immunopotentiating reconstituted influenza virosomes (IRIV) are used as the subunit antigen delivery system in the intranasal trivalent INFLEXAL™ product {Mischler & Metcalfe (2002) Vaccine 20 Suppl 5:B17-23} and the INFLUVAC PLUS™ product.

(2) Bacterial or microbial derivatives such as:

(a) Non-Toxic Derivatives of Enterobacterial Lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g. RC-529. See Johnson et al. (1999) Bioorg Med Chem Lett 9:2273-2278.

(b) Lipid A Derivatives

Lipid A derivatives include derivatives of lipid A from Escherichia coli such as OM-174. OM-174 is described for example in Meraldi et al., "OM-174, a New Adjuvant with a Potential for Human Use, Induces a Protective Response with Administered with the Synthetic C-Terminal Fragment 242-310 from the circumsporozoite protein of Plasmodium berghei", Vaccine (2003) 21:2485-2491; and Pajak, et al., "The Adjuvant OM-174 induces both the migration and maturation of murine dendritic cells in vivo", Vaccine (2003) 21:836-842.

(c) Immunostimulatory Oligonucleotides

Immunostimulatory oligonucleotides suitable for use as adjuvants include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla, et al., "Divergent synthetic nucleotide motif recognition pattern: design and development of potent immunomodulatory oligodeoxyribonucleotide agents with distinct cytokine induction profiles", Nucleic Acids Research (2003) 31(9): 2393-2400; WO02/26757 and WO99/62923 for examples of possible analog substitutions. The adjuvant effect of CpG oligonucleotides is further discussed in Krieg, "CpG motifs: the active ingredient in bacterial extracts?", Nature Medicine (2003) 9(7): 831-835; McCluskie, et al., "Parenteral and mucosal prime-boost immunization strategies in mice with hepatitis B surface antigen and CpG DNA", FEMS Immunology and Medical Microbiology (2002) 32:179-185; WO98/40100; U.S. Pat. Nos. 6,207,646; 6,239,116 and 6,429,199.

The CpG sequence may be directed to TLR9, such as the motif GTCGTT or TTCGTT. See Kandimalla, et al., "Toll-like receptor 9: modulation of recognition and cytokine induction by novel synthetic CpG DNAs", Biochemical Society Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell, et al., "CpG-A-Induced Monocyte IFN-gamma-Inducible Protein-10 Production is Regulated by Plasmacytoid Dendritic Cell Derived IFN-alpha", J. Immunol. (2003) 170(8):4061-4068; Krieg, "From A to Z on CpG", TRENDS in Immunology (2002) 23(2): 64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla, et al., "Secondary structures in CpG oligonucleotides affect immunostimulatory activity", BBRC (2003) 306:948-953; Kandimalla, et al., "Toll-like receptor 9: modulation of recognition and cytokine induction by novel synthetic GpG DNAs", Biochemical Society Transactions (2003) 31 (part 3):664-658; Bhagat et al., "CpG penta- and hexadeoxyribonucleotides as potent immunomodulatory agents" BBRC (2003) 300:853-861 and WO03/035836.

(3) Bioadhesives and mucoadhesives: Suitable bioadhesives include esterified hyaluronic acid microspheres (Singh et al. (2001) *J. Cont. Rele.* 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention. E.g. WO99/27960.

(4) Microparticles: Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

(5) Liposome formulations: Examples of liposome formulations suitable for use as adjuvants are described in U.S. Pat. Nos. 6,090,406, 5,916,588, and EP 0 626 169.

(6) Polyoxyethylene ethers and polyoxyethylene esters: Polyoxyethylene ethers and polyoxyethylene esters are described in, for example, WO99/52549. Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

(7) Polyphosphazene (PCPP): PCPP formulations are described, for example, in Andrianov et al., "Preparation of hydrogel microspheres by coacervation of aqueous polyphophazene solutions", Biomaterials (1998) 19(1-3):109-115 and Payne et al., "Protein Release from Polyphosphazene Matrices", Adv. Drug. Delivery Review (1998) 31(3):185-196.

(8) Imidazoquinoline Compounds: Examples of imidazoquinoline compounds suitable for use as adjuvants include Imiquimod and its analogues, described further in Stanley, Clin Exp Dermatol (2002) 27(7):571-577; Jones, Curr Opin Investig Drugs (2003) 4(2):214-218; and U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612.

(9) Thiosemicarbazone Compounds: Examples of thiosemicarbazone compounds, as well as methods of formulating, manufacturing, and screening for compounds all suitable for use as adjuvants include those described in WO04/60308.

(10) Tryptanthrin Compounds: Examples of tryptanthrin compounds, as well as methods of formulating, manufacturing, and screening for compounds all suitable for use as adjuvants in the invention include those described in WO04/64759.

(11) Human Immunomodulators: Human immunomodulators suitable for use as adjuvants include cytokines, such as interleukins (e.g. IL-1, IL-2, IL-4, IL-5, IL-6, IL-7, IL-12, etc.), interferons (e.g. interferon-γ), macrophage colony stimulating factor, and tumor necrosis factor.

Compositions of the invention may be formulated with one or more of the adjuvants identified above. For example, the following adjuvant compositions may be used in the invention:

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(1'-2'-dipalmitoyl-sn-glycero-3-huydroxyphosphoryloxy)-ethylamine (MTP-PE), etc.

Once formulated, the compositions of the invention can be administered directly to the subject (e.g., using one or more of the methods described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) (with or without the corresponding antigen) in liposomes, and direct microinjection of the DNA into nuclei.

The amount of DNA administered to the subject may vary depending on the antigens and/or delivery protocol. Thus, in certain embodiments, the amount of DNA used per administration (e.g., immunization) may vary from nanogram to microgram to milligram amounts of DNA, for example, as described in the Examples where the dose given is between about 2 nanograms to 20 micrograms or between about 2 nanograms and 10 milligrams. Further, as described below and shown in the Examples, multiple administrations of DNA (and/or protein) are contemplated.

Dosage treatment may be a single dose schedule or a multiple dose schedule. Administration of nucleic acids may also be combined with administration of peptides or other substances.

Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Generation of Synthetic Sequences

The synthetic sequences were generated from sequences obtained from HIVSF2 isolates. These sequences were manipulated to maximize expression of their gene products.

First, the HIV-1 codon usage pattern was modified so that the resulting nucleic acid coding sequence was comparable to codon usage found in highly expressed human genes. The HIV codon usage reflects a high content of the nucleotides A or T of the codon-triplet. The effect of the HIV-1 codon usage is a high AT content in the DNA sequence that results in a decreased translation ability and instability of the mRNA. In comparison, highly expressed human codons prefer the nucleotides G or C. The coding sequences were modified to be comparable to codon usage found in highly expressed human genes.

Certain Pol-encoding sequences were also modified in certain cases. For example, the protease (Prot) region of Pol was modified in certain sequences to that the protease activity was attenuated (constructs designated "pATT") or such that protease activity was inactivated (constructs designated "pIna").

The synthetic coding sequences were assembled by methods known in the art, for example by companies such as the Midland Certified Reagent Company (Midland, Tex.) or RetroGen (San Diego, Calif.) and cloned into the following eukaryotic expression vectors: pCMVlink or pCMVKm2. For a description of construction of these vectors, see, for example, WO 00/39302. Exemplary synthetic sequences are shown in FIGS. 1-2.

EXAMPLE 2

Expression Assays for the Synthetic Coding Sequences

The synthetic sequences are cloned into expression vectors in varying orientations.

Expression efficiencies for various vectors carrying the single or multiple synthetic sequences in various orientations are evaluated as follows. Cells from several mammalian cell lines (293, RD, COS-7, and CHO; all obtained from the American Type Culture Collection, 10801 University Boulevard, Manassas, Va. 20110-2209) are transfected with 2 μg of DNA in transfection reagent LT1 (PanVera Corporation, 545 Science Dr., Madison, Wis.). The cells are incubated for 5 hours in reduced serum medium (Opti-MEM, Gibco-BRL, Gaithersburg, Md.). The medium is then replaced with normal medium as follows: 293 cells, IMDM, 10% fetal calf serum, 2% glutamine (BioWhittaker, Walkersville, Md.); RD and COS-7 cells, D-MEM, 10% fetal calf serum, 2% glutamine (Opti-MEM, Gibco-BRL, Gaithersburg, Md.); and CHO cells, Ham's F-12, 10% fetal calf serum, 2% glutamine (Opti-MEM, Gibco-BRL, Gaithersburg, Md.). The cells are incubated for either 48 or 60 hours. Cell lysates are collected as described below in Example 3. Supernatants are harvested and filtered through 0.45 μm syringe filters. Supernatants are evaluated using the using 96-well plates coated with a rabbit polyclonal IgG directed against the appropriate HIV polypeptide (e.g., p24, p55, etc.). Biotinylated antibodies against HIV recognize the bound antigen. Conjugated strepavidin-horseradish peroxidase reacts with the biotin. Color develops from the reaction of peroxidase with TMB substrate. The reaction is terminated by addition of 4N $H_2SO4$. The intensity of the color is directly proportional to the amount of HIV antigen in a sample.

EXAMPLE 3

Western Blot Analysis of Expression

Human 293 cells were transfected as described in Example 2 with the constructs (all pCMV-based) containing the following sequences: synthetic Gag-encoding sequences; in-frame synthetic Gag- and Pol (inactivated)-encoding sequences; in-frame synthetic sequences, ordered 5' to 3', Gag-, Pol (inactivated)-, Tat-, Rev-, Nef-encoding sequences, in-frame synthetic sequences, ordered 5' to 3', Tat-, Rev-, Nef-, Gag-, Pol (inactivated)-encoding sequences; in-frame synthetic Gag- and Pol (attenuated)-encoding sequences; in-frame synthetic sequences, ordered 5' to 3', Gag-, Pol (attenuated)-, Tat-, Rev-, Nef-encoding sequences; and in-frame synthetic sequences, ordered 5' to 3', Tat-, Rev-, Nef-, Gag-, Pol (attenuated)-encoding sequences.

Cells were cultivated for 48 or 72 hours post-transfection. Cell lysates were prepared as follows. The cells were washed once with phosphate-buffered saline, lysed with detergent [1% NP40 (Sigma Chemical Co., St. Louis, Mo.) in 0.1 M Tris-HCl, pH 7.5], and the lysate transferred into fresh tubes. Supernatants were prepared as previously described and 20 μl of supernatant loaded in reduced condition into a Tris-bis gel and run with MES running buffer.

SDS-polyacrylamide gels (pre-cast 8-16%; Novex, San Diego, Calif.) were loaded with 20 μl of supernatant or 10 μl of cell lysate. A protein standard was also loaded (5 μl, broad size range standard; BioRad Laboratories, Hercules, Calif.). Electrophoresis was carried out and the proteins were transferred using a BioRad Transfer Chamber (BioRad Laboratories, Hercules, Calif.) to Immobilon P membranes (Millipore Corp., Bedford, Mass.) using the transfer buffer recommended by the manufacturer (Millipore), where the transfer is performed at 100 volts for 90 minutes. The membranes are exposed to HIV-1-positive human patient serum (1:400 dilution) and anti-β actin (dilution 1:5000) for 1 hr at room temperature. Anti-mouse and anti-human antibodies (1:30000 dilution) were used for detection using Odyssey™ Antibody Detection Kits (Li-Cor Biosciences, Lincoln, Nebr.), following the manufacturer's instructions.

Figure 4:
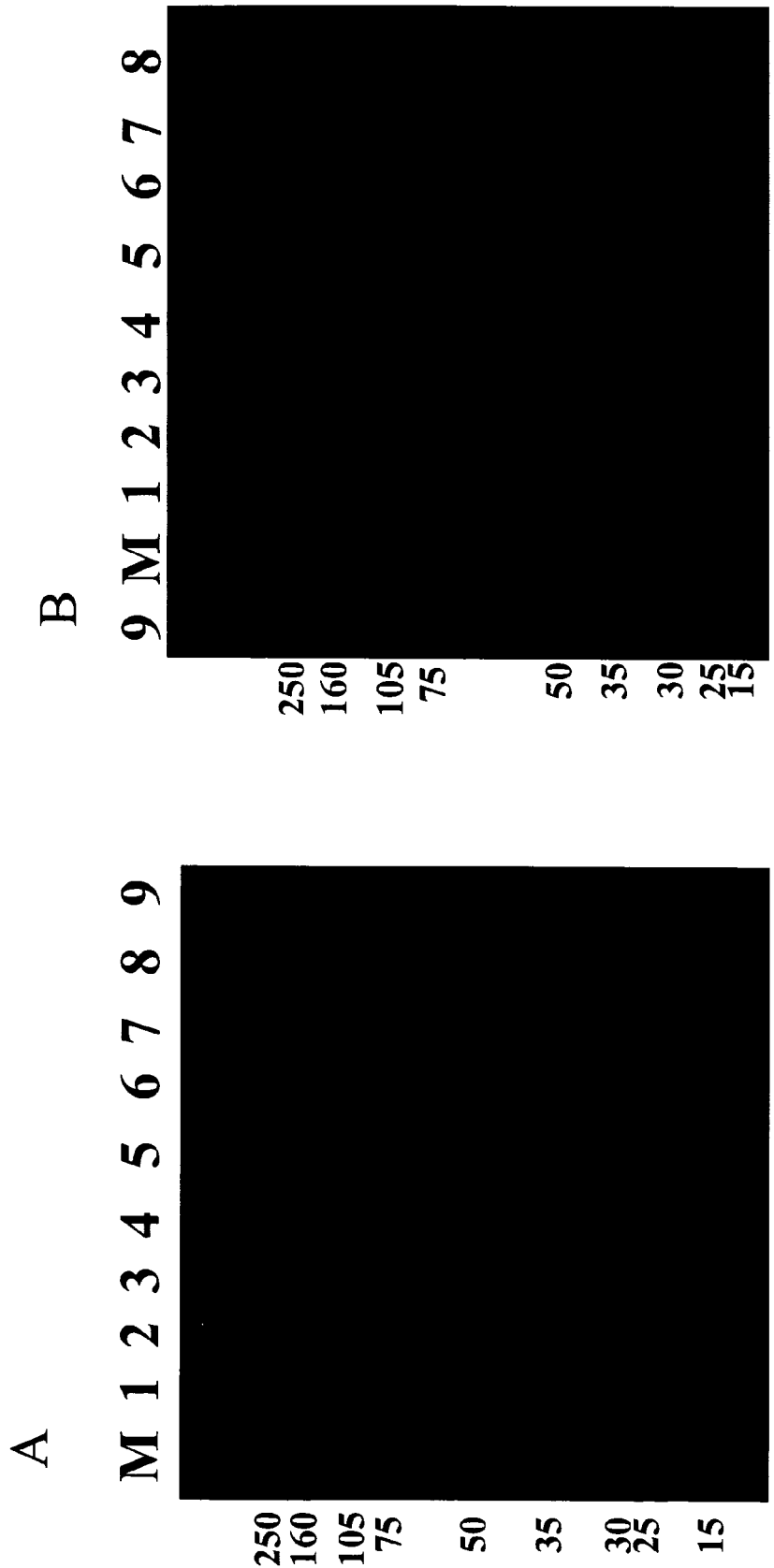
FIG. 4, panels A and B, are reproductions of gels showing Western Blot analysis of protein levels in supernatants of cells transfected with various HIV polypeptide-encoding constructs. Lane designations are the same as in FIG. 3, except the protein levels are measured from supernatant not lysate.

In the experiments shown in FIGS. 3 and 4, synthetic HIV polypeptide encoding sequences (e.g., in expression cassettes) in which Tat, rev and/or nef were positioned 5' to Gag- and Pol-encoding sequences exhibited increased production of their protein products, relative to wild-type and to synthetic sequences in which Tat, rev and/or nef were positioned 3' to Gag- and Pol-encoding sequences. (FIG. 3, especially comparing lane 3 to lane 4 and lane 6 to lane 7) and supernatants (FIG. 4, especially comparing lane 3 to lane 4 and lane 6 to lane 7).

Figure 5:
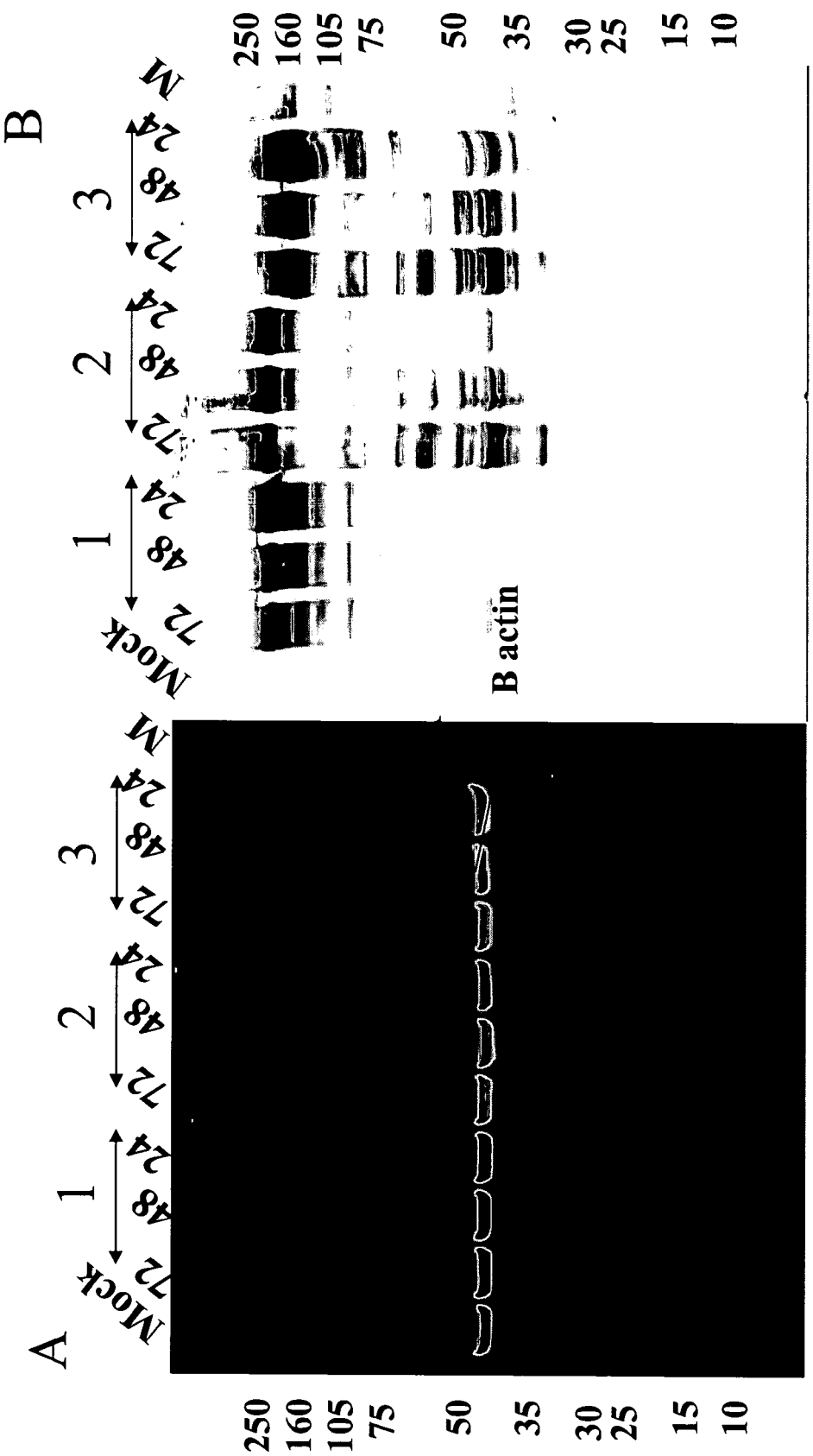
FIG. 5, panels A and B, are reproductions of gels showing Western Blot analysis of protein levels in lysates of cells transfected with various HIV polypeptide-encoding constructs. Lanes designated "72," "48," or "24" refer to the time point (in hours) at which the experiments were conducted. Lanes designated "1" show results from a construct (pCMVKM2TRN5'gCpIna) encoding a Gag, Pol (inactivated), Tat, rev and nef polyprotein, in which Tat, rev and nef sequences are 5' to the Gag and Pol encoding sequences. Lanes designated with a "2" show results from a construct (pCMVKM2gCpInaTRN3') encoding a Gag, Pol (inactivated), Tat, rev and nef polyprotein, in which Tat, rev and nef sequences are 3' to the Gag and Pol encoding sequences. Lanes designated with a "3" show results from a construct (pCMVKM2gCpIna) encoding a Gag and Pol (inactivated) polyprotein.
Figure 6:
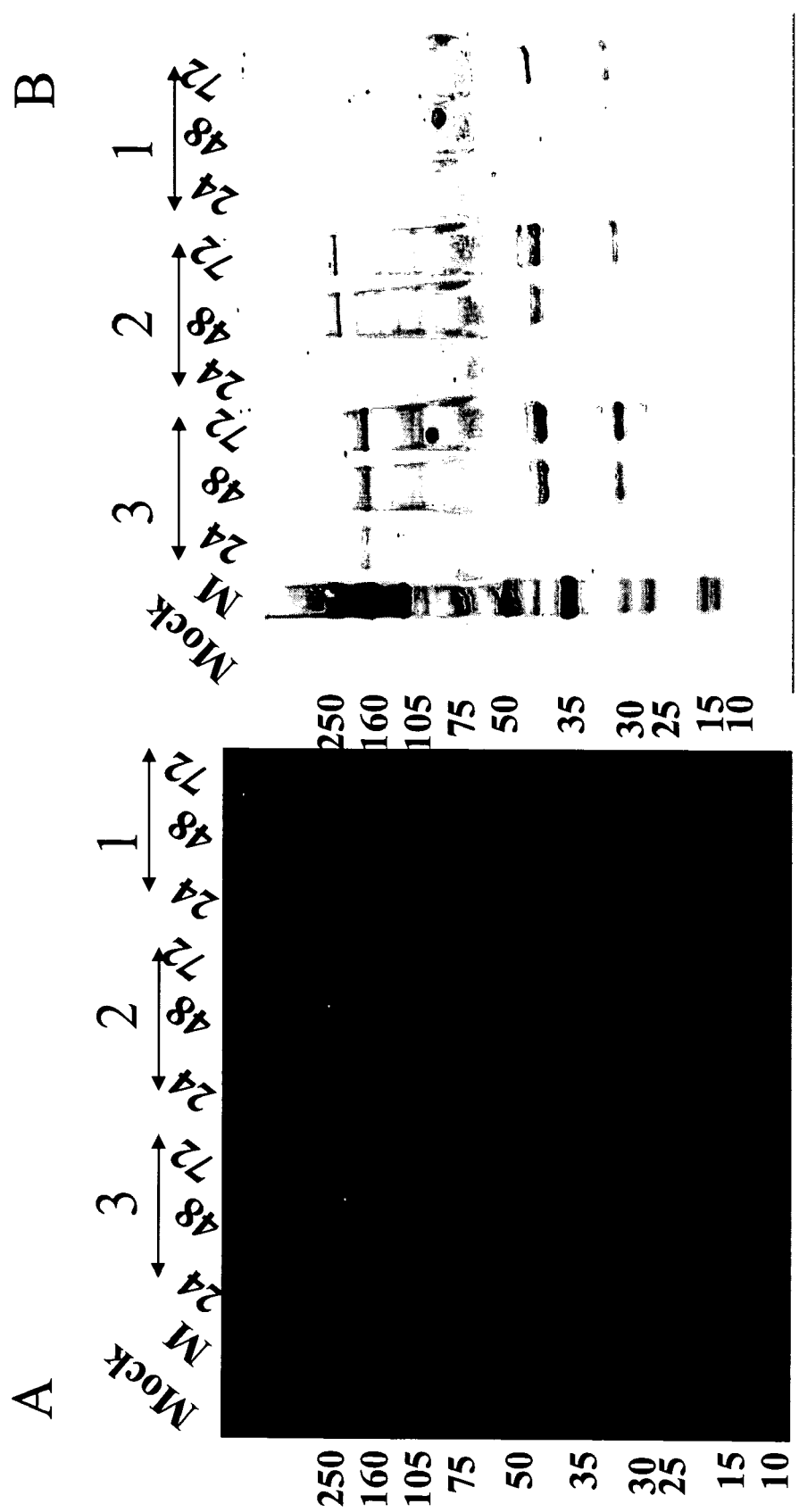
FIG. 6, panels A and B, are reproductions of gels showing Western Blot analysis of protein levels in supernatants of cells transfected with various HIV polypeptide-encoding constructs. Lane designations are the same as in FIG. 5, except the protein levels are measured from supernatant not lysate.

FIGS. 5 and 6 show similar experiments in which increased expression of Gag and/or pol from constructs in which Tat, rev and/or nef were positioned 5' to Gag- and Pol-encoding sequences was not observed.

EXAMPLE 4

In Vivo Immunogenicity of Synthetic HIV Expression Cassettes

A. Immunization

To evaluate the immunogenicity of the synthetic HIV expression cassettes, mouse studies were performed as follows. The plasmid DNA, e.g., pCMVKM2 carrying an expression cassette comprising a synthetic sequence of the present invention, was diluted to the following final concentrations in a total injection volume of 100 μl: 20 μg, 2 μg, 0.2 μg, and 0.02 μg. In particular 18 groups of 4 animals and 1 group of 3 animals were immunized as shown in the following Table. In all Groups, the route of administration was intramuscular injection into the tibialis anterior.

both legs (50 μl per leg=100 μl total per animal), according the following immunization schedule.

| | GROUPS 1-18 | GROUPS 1-18 |
|---|---|---|
| | Immunization: | |
| | 1 | 2 |
| | Weeks: | |
| Group | 0 | 4 |
| 1 | pCMV-TRN | pCMV-TRN |
| 2 | pCMV-TRN | pCMV-TRN |
| 3 | pCMV-TRN | pCMV-TRN |
| 4 | pCMV-gagCpollna | pCMV-gagCpollna |
| 5 | | |
| 6 | pCMV-gagCpollna | pCMV-gagCpollna |
| 7 | pCMV-TRN + gagCpollna | pCMV-TRN + gagCpollna |
| 8 | pCMV-TRN + gagCpollna | pCMV-TRN + gagCpollna |
| 9 | | |
| 10 | pCMV-TRNgagCpollna | pCMV-TRNgagCpollna |
| 11 | pCMV-TRNgagCpollna | pCMV-TRNgagCpollna |
| 12 | pCMV-TRNgagCpollna | pCMV-TRNgagCpollna |
| 13 | gagCpollnaTRN | gagCpollnaTRN |
| 14 | gagCpollnaTRN | gagCpollnaTRN |
| 15 | gagCpollnaTRN | gagCpollnaTRN |
| 16 | pCMV-Tat + gagCpollna | pCMV-Tat + gagCpollna |
| 17 | | |
| 18 | pCMV-Tat + gagCpollna | pCMV-Tat + gagCpollna |

To overcome possible negative dilution effects of the diluted DNA, the total DNA concentration in each sample was brought up to 20 μg using the vector (pCMVKM2) alone. Alphavirus vectors (e.g., Sindbis) comprising the same sequences are also prepared. Controls (wild type or unicistronic synthetic sequences) were handled in the same manner.

| Grp. No. | Anim./grp | Animal No. | # of Immunizations | Immunogen | Total Dose | Total Vol. | Vol/Site | Sites/Animal |
|---|---|---|---|---|---|---|---|---|
| 1 | 4 | 1-4 | 2 | pCMV-TRN | 20 ug | 100 μl | 50 μl | 2 |
| 2 | 4 | 5-8 | 2 | pCMV-TRN | 2 ug | 100 μl | 50 μl | 2 |
| 3 | 4 | 9-12 | 2 | pCMV-TRN | 0.2 ug | 100 μl | 50 μl | 2 |
| 4 | 4 | 13-16 | 2 | pCMV-gagCpollna | 20 ug | 100 μl | 50 μl | 2 |
| 5 | 4 | 17-20 | 2 | pCMV-gagCpollna | 2 ug | 100 μl | 50 μl | 2 |
| 6 | 4 | 21-24 | 2 | pCMV-gagCpollna | 0.2 ug | 100 μl | 50 μl | 2 |
| 7 | 4 | 25-28 | 2 | pCMV-TRN + gagCpollna | 20 ug | 100 μl | 50 μl | 2 |
| 8 | 4 | 29-32 | 2 | pCMV-TRN + gagCpollna | 2 ug | 100 μl | 50 μl | 2 |
| 9 | 4 | 33-36 | 2 | pCMV-TRN + gagCpollna | 0.2 ug | 100 μl | 50 μl | 2 |
| 10 | 4 | 37-40 | 2 | pCMV-TRNgagCpollna | 20 ug | 100 μl | 50 μl | 2 |
| 11 | 4 | 41-44 | 2 | pCMV-TRNgagCpollna | 2 ug | 100 μl | 50 μl | 2 |
| 12 | 4 | 45-48 | 2 | pCMV-TRNgagCpollna | 0.2 ug | 100 μl | 50 μl | 2 |
| 13 | 4 | 49-52 | 2 | pCMV-gagCpollnaTRN | 20 ug | 100 μl | 50 μl | 2 |
| 14 | 4 | 53-56 | 2 | pCMV-gagCpollnaTRN | 2 ug | 100 μl | 50 μl | 2 |
| 15 | 4 | 57-60 | 2 | pCMV-gagCpollnaTRN | 0.2 ug | 100 μl | 50 μl | 2 |
| 16 | 4 | 61-64 | 2 | pCMV-Tat + gagCpollna | 20 ug | 100 μl | 50 μl | 2 |
| 17 | 4 | 65-68 | 2 | pCMV-Tat + gagCpollna | 2 ug | 100 μl | 50 μl | 2 |
| 18 | 4 | 69-72 | 2 | pCMV-Tat + gagCpollna | 0.2 ug | 100 μl | 50 μl | 2 |
| 19 | 3 | 73-75 | 2 | naive | — | — | — | — |

On the day of injection one 100 μl vial of plasmid was used, with 50 μl injected IM into the tibialis anterior (TA) muscle of To test immune responses, animals were bled according to the following schedule:

| All 19 Groups | |
|---|---|
| Bleed: | 1 |
| Week: | 6 |
| Sample: | Clotted Bld. for Serum |
| Volume: | 200 µl |
| Method: | TB/SO |

B. Humoral Immune Response

Figure 7:
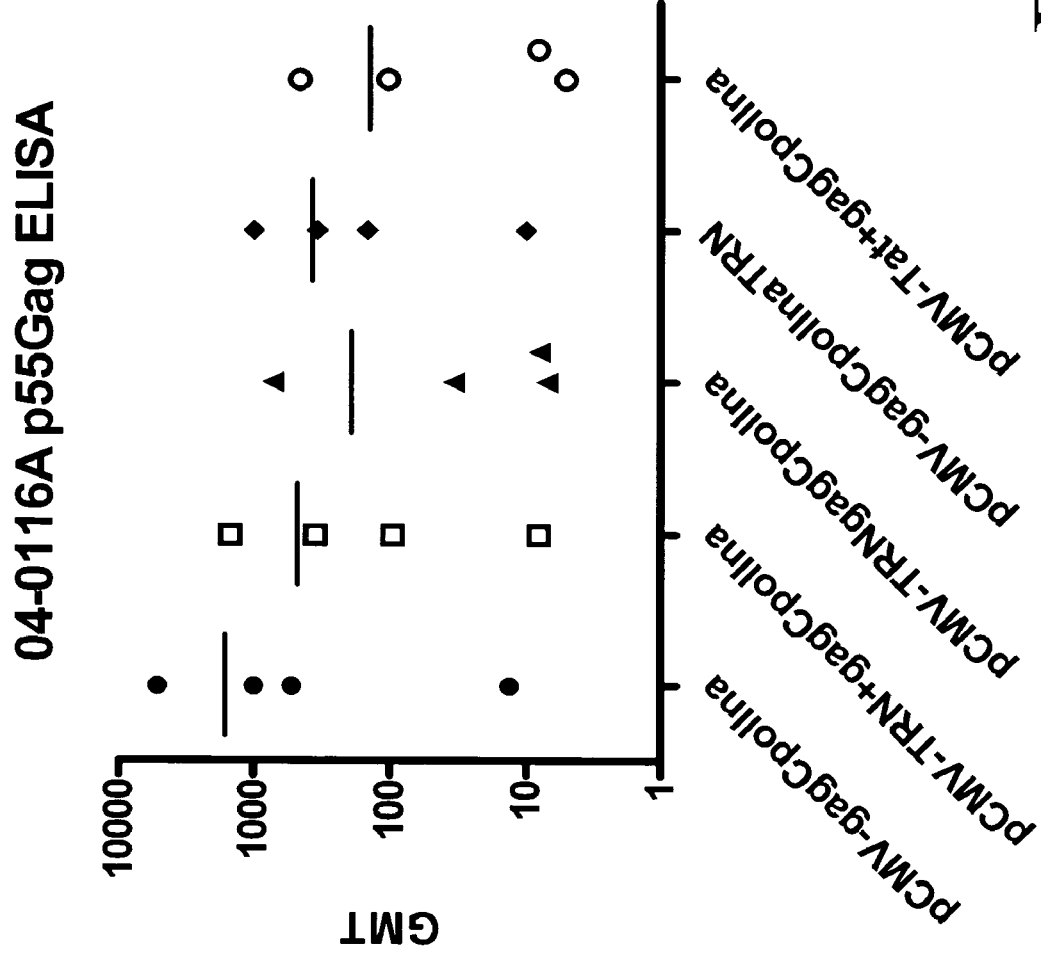
FIG. 7 is a graph depicting results of Gag ELISAs of mouse bleeds following administration to the animals of the constructs listed. Constructs pCMV-gagCpolIna, pCMV-TRNgagCpolIna and pCMV-gagCpolInaTRN refer to polycistronic constructs expressing, respectively, a Gag and inactivated Pol polyprotein, a Tat, rev, nef, Gag, and inactivated Pol polyprotein, and a Gag, inactivate Pol, Tat, rev, nef polyprotein. Constructs pCMV-TNR+gagCpolIna and pCMV-Tat+gagCpolIna refer to constructs which express Gag and inactivated Pol separately from either a Tat, rev, nef polyprotein (TRN) or tat.

Humoral immune responses were checked with a suitable anti-HIV antibody ELISAs (enzyme-linked immunosorbent assays). Briefly, sera from immunized mice were screened for antibodies directed against an appropriate HIV protein (e.g., HIV p55 for Gag). ELISA microtiter plates were coated with 0.2 µg of HIV protein per well overnight and washed four times; subsequently, blocking was done with PBS-0.2% Tween (Sigma) for 2 hours. After removal of the blocking solution, 100 µl of diluted mouse serum was added. Sera are tested at 1/25 dilutions and by serial 3-fold dilutions, thereafter. Microtiter plates were washed four times and incubated with a secondary, peroxidase-coupled anti-mouse IgG antibody (Pierce, Rockford, Ill.). ELISA plates were washed and 100 µl of 3,3',5,5'-tetramethyl benzidine (TMB; Pierce) was added per well. The optical density of each well was measured after 15 minutes. The titers reported are the reciprocal of the dilution of serum that gave a half-maximum optical density (O.D.). Results are shown in FIG. 7.

C. Cellular Immune Response

Intracellular cytokine staining (ICS) for Gag and Pol-specific IFN-g-producing CD8+ lymphocytes was performed essentially as described in zur Megede et al. (2003) *J. Virol.* 77(11):6197-6207 and zur Megede et al. (2000) *J. Virol.* 74:2628-2635. Briefly, spleens were harvested two weeks post-second DNA immunization or five days post recombinant vaccinia challenge and single cell suspensions were prepared. 1×10$^6$ nucleated spleen cells were cultured in duplicate at 37° C. in the presence or absence of 10 µg/ml p7g peptide for Gag. Unstimulated cells plus spleen cells from naive mice were used as background and negative controls. The background values were generally very low, between 0.01 and 0.1% of IFN-g secreting CD8+ cells.

Figure 8:
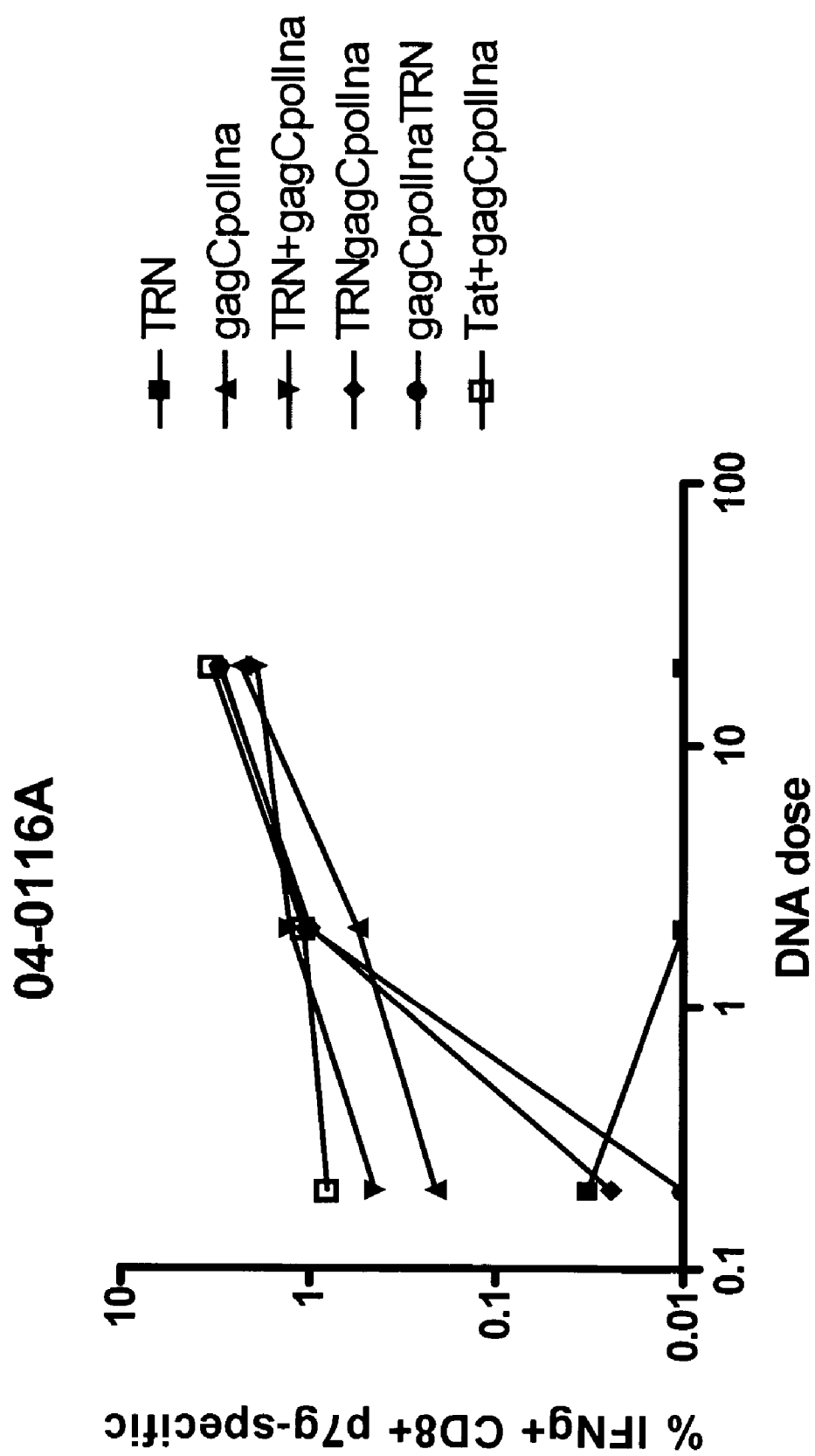
FIG. 8 is a graph depicting results of cellular immune responses (% of IFN-gamma secreting CD8 T cells), as measured by intracellular cytokine staining (FACS-flow cytometry) assay, to the same constructs as shown in FIG. 7.

After 5 hours, cells were washed, incubated with anti-CD16/32 (Pharmingen, San Diego, Calif.) to block Fcg receptors, and fixed in 1% (w/v) paraformaldehyde and stored overnight at 4° C. The following day cells were stained with FITC-conjugated CD8 mAb (Pharmingen), washed, treated with 0.5% (w/v) Saponin (Sigma) and then incubated with phycoerythrin (PE)-conjugated mouse IFN-g mAb (Pharmingen) in the presence of 0.1% (w/v) saponin. Cells were then washed and analyzed on a FACSCalibur flow cytometer (Becton-Dickinson Immunocytometry Systems, San Jose, Calif.). Results are shown in FIG. 8.

Cellular immune responses are also tested by 1) CTL bulk culture and $^{51}$Cr-relase 2) lymphoproliferation, and 3) ELISPOT. (See, also, Cherpelis et al. (2001) *Immunol. Lett.* 79:47-55 (describing LPA assays); and Vajdy et al. (2001) *J. Infect Dis* 15;184(12):1613-1616 (describing ELISPOT)).

EXAMPLE 5

In Vivo Immunogenicity of Synthetic HIV Expression Cassettes

A. General Immunization Methods

To evaluate the immunogenicity of the synthetic HIV expression cassettes, studies using guinea pigs, rabbits, mice, rhesus macaques and baboons are performed. The studies are typically structured as follows: DNA immunization alone (single or multiple); DNA immunization followed by protein immunization (boost); DNA immunization followed by Sindbis particle immunization; immunization by Sindbis particles alone.

B. Guinea Pigs

Experiments may be performed using guinea pigs as follows. Groups comprising six guinea pigs each are immunized intramuscularly or mucosally at 0, 4, and 12 weeks with plasmid DNAs encoding expression cassettes comprising one or more the sequences described herein. The animals are subsequently boosted at approximately 18 weeks with a single dose (intramuscular, intradermally or mucosally) of the HIV protein encoded by the sequence(s) of the plasmid boost and/or other HIV proteins. Antibody titers (geometric mean titers) are measured at two weeks following the third DNA immunization and at two weeks after the protein boost. These results are used to demonstrate the usefulness of the synthetic constructs to generate immune responses, as well as, the advantage of providing a protein boost to enhance the immune response following DNA immunization.

C. Rabbits

Experiments may be performed using rabbits as follows. Rabbits are immunized intramuscularly, mucosally, or intradermally (using a Bioject needless syringe) with plasmid DNAs encoding the HIV proteins described herein. The nucleic acid immunizations are followed by protein boosting after the initial immunization. Typically, constructs comprising the synthetic HIV-polypeptide-encoding polynucleotides of the present invention are highly immunogenic and generate substantial antigen binding antibody responses after only 2 immunizations in rabbits.

D. Baboons

Four baboons are immunized 3 times (weeks 0, 4 and 8) bilaterally, intramuscular into the quadriceps or mucosally using the gene delivery vehicles described herein.

Lymphoproliferative responses to are observed in baboons two weeks post-fourth immunization (at week 14), and enhanced substantially post-boosting with HIV-polypeptide (at week 44 and 76). Such proliferation results are indicative of induction of T-helper cell functions.

The animals are also bled two weeks after each immunization and an HIV antibody ELISA is performed with isolated plasma. The ELISA is performed essentially as described above except the second antibody-conjugate is an anti-human IgG, g-chain specific, peroxidase conjugate (Sigma Chemical Co., St. Louis, Md. 63178) used at a dilution of 1:500. Fifty µg/ml yeast extract may be added to the dilutions of plasma samples and antibody conjugate to reduce non-specific background due to preexisting yeast antibodies in the baboons.

E. Rhesus Macagues

The improved immunogenic potency of the synthetic, codon-modified HIV-polypeptide encoding polynucleotides of the present invention, when constructed into expression plasmids may be confirmed in rhesus macaques. Typically, the macaques have detectable HIV-specific CTL after two or three 1 mg doses of modified HIV polynucleotide. In sum, these results demonstrate that the synthetic HIV DNA is immunogenic in non-human primates. Neutralizing antibodies may also detected.

F. Immune Responses

Cellular and humoral immune responses were evaluated in mice (essentially as described in Example 4) for the following constructs: TatRefNef (TRN), GagcPolIna, GagcPolTatRef-Nef (gCpInaTRN3), TatRefNefGagcPolIna (5TRNgCpIna), GagcPolatt (gCpAtt), GagcPolAttTatRefNef (gCpAttTRN3), and TatRevNefGagcPolAtt (5TRNgCpIna).

As summarized in Examples 2 and 3, in vitro expression certain data showed increased expression of Gag-Pol proteins (e.g., p24 and, p55Gag and p66RT) using polycistronic constructs in which Tat, Ref and Nef were positioned 5' to Gag and Pol. (FIGS. 3 and 4). Other data showed no increased expression based on the relative positions of the nucleotides (FIGS. 5 and 6).

Previous studies have shown that the immune response in mammalian subjects correlates with the relative levels of protein expression. See, e.g., U.S. Pat. No. 6,602,705 and International Publications WO 00/39303, WO 00/39302, WO 00/39304, WO 02/04493. Therefore, it is expected that 5TRNgCpIna and 5TRNgCpAtt will generate robust immune responses in vivo.

Although preferred embodiments of the subject invention have been described in some detail, it is understood that obvious variations can be made without departing from the spirit and the scope of the invention.

What is claimed is:

1. A vector comprising a synthetic polynucleotide comprising polynucleotide sequences encoding a polyprotein comprising HIV Gag, Pol, Tat, Rev and Nef polypeptides, wherein the polynucleotide sequence is operably linked to control elements, wherein the polynucleotide sequences encoding Gag and Pol polypeptides are located 3' to polynucleotide sequences encoding the Tat, Rev, and Nef polypeptides, wherein expression of the polynucleotide sequence is increased relative to expression of a native polynucleotide sequence encoding the polypeptides.

2. The vector of claim 1, wherein the polynucleotide sequences comprise sequences from a subtype B strain of HIV.

3. The vector of claim 1, wherein the synthetic polynucleotide sequence comprises one or more mutations that affect one or more functions of one or more of the encoded HIV polypeptides.

4. The vector of claim 3, wherein the mutation comprises a mutation that attenuates or inactivates the protease region of the Pol polypeptide.

5. The vector of claim 1, comprising SEQ ID NO:1.

6. The vector of claim 1, further comprising sequences encoding additional polypeptides.

7. The vector of claim 6, wherein the additional polypeptides are selected from the group consisting of coding sequences for hepatitis B, hepatitis C, HIV Env, HIV Vif, HIV Vpr, HIV Vpu, and cytokines.

8. The vector of claim 1, wherein the vector comprises an alphavirus vector construct.

9. The vector of claim 8, wherein the wherein the alphavirus vector construct is a cDNA vector construct.

10. The vector of claim 1, wherein the vector is a nonviral vector.

11. The vector of claim 1, wherein the vector is a viral vector.

12. The vector of claim 11 wherein the viral vector is a retroviral vector.

13. The vector of claim 11, wherein the viral vector is a lentiviral vector.

14. A method of producing HIV proteins, the method comprising:
(1) expressing the polyprotein from the vector of claim 1 in a host cell; and
(2) isolating the polyprotein.

15. An isolated cell comprising the vector of claim 1.

16. The isolated cell of claim 15, wherein the cell is a mammalian cell.

17. The isolated cell of claim 16, wherein the cell is selected from the group consisting of BHK, VERO, HT1080, 293, RD, COS-7, and CHO cells.

18. The isolated cell of claim 17, wherein the cell is a CHO cell.

19. The isolated cell of claim 15, wherein the cell is an insect cell.

20. The isolated cell of claim 19, wherein the cell is either Trichoplusia ni (Tn5) or Sf9 insect cells.

21. The isolated cell of claim 15, wherein the cell is a bacterial cell.

22. The isolated cell of claim 15, wherein the cell is a yeast cell.

23. The isolated cell of claim 15, wherein the cell is a plant cell.

24. The isolated cell of claim 15, wherein the cell is an antigen presenting cell.

25. The isolated cell of claim 24, wherein the antigen presenting cell is a lymphoid cell selected from the group consisting of macrophage, monocyte, dendritic cells, B-cells, T-cells, stem cells, and progenitor cells thereof.

26. The isolated cell of claim 15, wherein the cell is an immortalized cell.

27. The isolated cell of claim 15, wherein the cell is a tumor-derived cell.

28. A recombinant expression system for use in a selected host cell, comprising, a cell of claim 15, wherein the control elements of the vector are compatible with expression in the selected host cell.

29. The recombinant expression system of claim 28, wherein the control elements are selected from the group consisting of a transcription promoter, a transcription enhancer element, a transcription termination signal, polyadenylation sequences, sequences for optimization—of initiation of translation, and translation termination sequences.

30. The recombinant expression system of claim 29, wherein the transcription promoter is selected from the group consisting of CMV, CMV+intron A, SV40, RSV, HIV-Ltr, MMLV-ltr, and metallothionein.

31. A composition comprising the vector of claim 1 and one or more adjuvants.

32. The composition of claim 31 further comprising one or more polypeptides.

* * * * *

UNITED STATES PATENT AND TRADEMARK OFFICE
CERTIFICATE OF CORRECTION

| | | |
|---|---|---|
| PATENT NO. | : 7,622,125 B2 | Page 1 of 1 |
| APPLICATION NO. | : 11/124602 | |
| DATED | : November 24, 2009 | |
| INVENTOR(S) | : Zur Megede et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 647 days.

Signed and Sealed this
Eleventh Day of January, 2011

David J. Kappos
*Director of the United States Patent and Trademark Office*